US011413459B2

(12) United States Patent
Raschella et al.

(10) Patent No.: US 11,413,459 B2
(45) Date of Patent: Aug. 16, 2022

(54) SYSTEM FOR PLANNING AND/OR PROVIDING NEUROSTIMULATION FOR A PATIENT

(71) Applicants: ECOLE POLYTECHNIQUE FEDERALE DE LAUSANNE (EPFL), Lausanne (CH); ONWARD MEDICAL N.V., Eindhoven (NL)

(72) Inventors: Flavio Raschella, Lausanne (CH); Silvestro Misera, Geneva (CH); Gregoire Courtine, Lausanne (CH); Tomislav Milekovic, Geneva (CH); Fabien Wagner, Lausanne (CH); Marco Capogrosso, Lausanne (CH); Jurriaan Bakker, Eindhoven (NL); Robin Brouns, Eindhoven (NL); Vincent Delattre, Eindhoven (NL)

(73) Assignees: ECOLE POLYTECHNIQUE FEDERALE DE LAUSANNE (EPFL), Lausanne (CH); ONWARD MEDICAL B.V., Eindhoven (NL)

( * ) Notice: Subject to any disclaimer, the term of this patent is extended or adjusted under 35 U.S.C. 154(b) by 68 days.

(21) Appl. No.: 16/769,519

(22) PCT Filed: Nov. 29, 2018

(86) PCT No.: PCT/EP2018/082946
§ 371 (c)(1),
(2) Date: Jun. 3, 2020

(87) PCT Pub. No.: WO2019/110401
PCT Pub. Date: Jun. 13, 2019

(65) Prior Publication Data
US 2020/0384272 A1 Dec. 10, 2020

(30) Foreign Application Priority Data

Dec. 5, 2017 (EP) .................................... 17205362

(51) Int. Cl.
A61N 1/36 (2006.01)
A61B 5/389 (2021.01)

(52) U.S. Cl.
CPC .......... *A61N 1/36139* (2013.01); *A61B 5/389* (2021.01); *A61N 1/36062* (2017.08)

(58) Field of Classification Search
CPC ............ A61N 1/36139; A61N 1/36062; A61N 1/36067; A61B 5/389; A61B 5/4836; G16H 20/30; G16H 50/50
See application file for complete search history.

(56) References Cited

U.S. PATENT DOCUMENTS

2015/0066111 A1 3/2015 Blum et al.
2016/0001096 A1 1/2016 Mishelevich
(Continued)

FOREIGN PATENT DOCUMENTS

EP 2810689 A1 12/2014
EP 2810690 A1 12/2014

OTHER PUBLICATIONS

Capogrosso, M., Milekovic, T., Borton, D., Wagner, F., Moraud, E. M., Mignardot, J. B., Buse, N., Gandar, J., Barraud, Q., Xing, D., Rey, E., Duis, S., Jianzhong, Y., Ko, W. K. D., Li, Q., Detemple, P., Denison, T., Micera, S., Bezard, E., . . . Courtine, G. (2016). A brain-spine interface alleviatin (Year: 2016).*

(Continued)

Primary Examiner — Paula J Stice
(74) Attorney, Agent, or Firm — McCoy Russell LLP

(57) ABSTRACT

The present invention relates to systems and methods for planning and/or providing neurostimulation for a patient. An example system includes
a pathological spinal cord map storage module for storing at least one pathological spinal cord map describing activation of a spinal cord of a patient, (Continued)

a healthy spinal cord map storage module for storing at least one reference map describing physiological activation of the spinal cord of at least one healthy subject, an analysis module for generating a deviation map, the deviation map describing an activation difference between the pathological spinal cord map and the reference map, and a compensation module for calculating, based on the deviation map, a neurostimulation protocol for compensating the activation difference.

15 Claims, 11 Drawing Sheets

(56) References Cited

U.S. PATENT DOCUMENTS

| | | |
|---|---|---|
| 2016/0030750 A1 | 2/2016 | Bokil et al. |
| 2016/0279418 A1 | 9/2016 | Courtine et al. |
| 2017/0173326 A1* | 6/2017 | Bloch ............... A61N 1/36067 |

OTHER PUBLICATIONS

Bizzi, E. et al., "Modular Organization of Motor Behavior," Trends in Neurosciences, vol. 18, No. 10, Oct. 1995, 8 pages.

Rattay, F. et al., "Epidural electrical stimulation of posterior structures of the human lumbosacral cord: 2. quantitative analysis by computer modeling," Spinal Cord, vol. 38, No. 8, Aug. 2000, 17 pages.

Minassian, K. et al., "Stepping-like movements in humans with complete spinal cord injury induced by epidural stimulation of the lumbar cord: electromyographic study of compound muscle action potentials," Spinal Cord, vol. 42, No. 7, Jul. 2004, Published Online May 4, 2004, 16 pages.

Gerasimenko, Y. et al., "Spinal cord reflexes induced by epidural spinal cord stimulation in normal awake rats," Journal of Neuroscience Methods, vol. 157, No. 2, Oct. 30, 2006, Published Online Jun. 9, 2006, 11 pages.

Courtine, G. et al., "Transformation of nonfunctional spinal circuits into functional states after the loss of brain input," Nature Neuroscience, vol. 12, No. 10, Oct. 2009, Published Online Sep. 20, 2009, 12 pages.

Harkema, S. et al., "Effect of Epidural stimulation of the lumbosacral spinal cord on voluntary movement, standing, and assisted stepping after motor complete paraplegia: a case study," Lancet, vol. 377, No. 9781, Jun. 4, 2011, Available Online May 19, 2011, 17 pages.

Van Den Brand, R. et al., "Restoring Voluntary Control of Locomotion after Paralyzing Spinal Cord Injury," Science Magazine, vol. 336, No. 6085, Jun. 1, 2012, 5 pages.

Capogrosso, M. et al., "A Computational Model for Epidural Electrical Stimulation of Spinal Sensorimotor Circuits," Journal of Neuroscience, vol. 33, No. 49, Dec. 4, 2013, 15 pages.

Levine, A. et al., "Identification of cellular node for motor control pathways," Nature Neuroscience, vol. 17, No. 4, Apr. 2014, Available Online Mar. 9, 2014, 22 pages.

Angeli, C. et al., "Altering spinal cord excitability enables voluntary movements after chronic complete paralysis in humans," Brain: A Journal of Neurology, vol. 137, No. 5, May 1, 2014, Published Online Apr. 8, 2014, 16 pages.

Wenger, N. et al., "Closed-loop neuromodulation of spinal sensorimotor circuits controls refined locomotion after complete spinal cord injury," Science Translational Medicine, vol. 6, No. 255, Sep. 24, 2014, 12 pages.

Danner, S. et al., "Human spinal locomotor control is based on flexibly organized burst generators," Brain: A Journal of Neurology, vol. 138, No. 3, Mar. 1, 2015, Published Online Jan. 12, 2015, 12 pages.

Shamir, R. et al., "Machine learning approach to optimizing combined stimulation and medication therapies for Parkinson's disease," Brain Stimulation, vol. 8, No. 6, Nov. 2015, Published Online Jun. 15, 2015, 22 pages.

Gerasimenko, Y. et al., "Noninvasive Reactivation of Motor Descending Control after Paralysis," Journal of Neurotrauma, vol. 32, No. 24, Dec. 15, 2015, Published Online Aug. 20, 2015, 13 pages.

Wenger, N. et al., "Spatiotemporal neuromodulation therapies engaging muscle synergies improve motor control after spinal cord injury," Natural Medicine, vol. 22, No. 2, Feb. 2016, Available Online Jan. 18, 2016, 33 pages.

Moraud, E. et al., "Mechanisms Underlying the Neuromodulation of Spinal Circuits for Correcting Gait and Balance Deficits after Spinal Cord Injury," Neuron, vol. 89, No. 4, Feb. 17, 2016, Available Online Feb. 4, 2016, 16 pages.

Capogrosso, M. et al., "A Brain-Spinal Interface Alleviating Gait Deficits after Spinal Cord Injury in Primates," Nature, vol. 539, No. 7628, Nov. 10, 2016, 39 pages.

ISA European Patent Office, International Search Report and Written Opinion Issued in Application No. PCT/EP2018/082946, dated Jan. 28, 2019, WIPO, 11 pages.

* cited by examiner

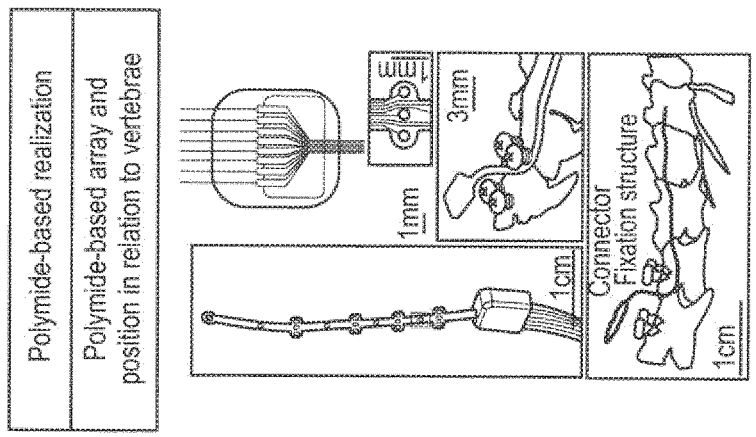
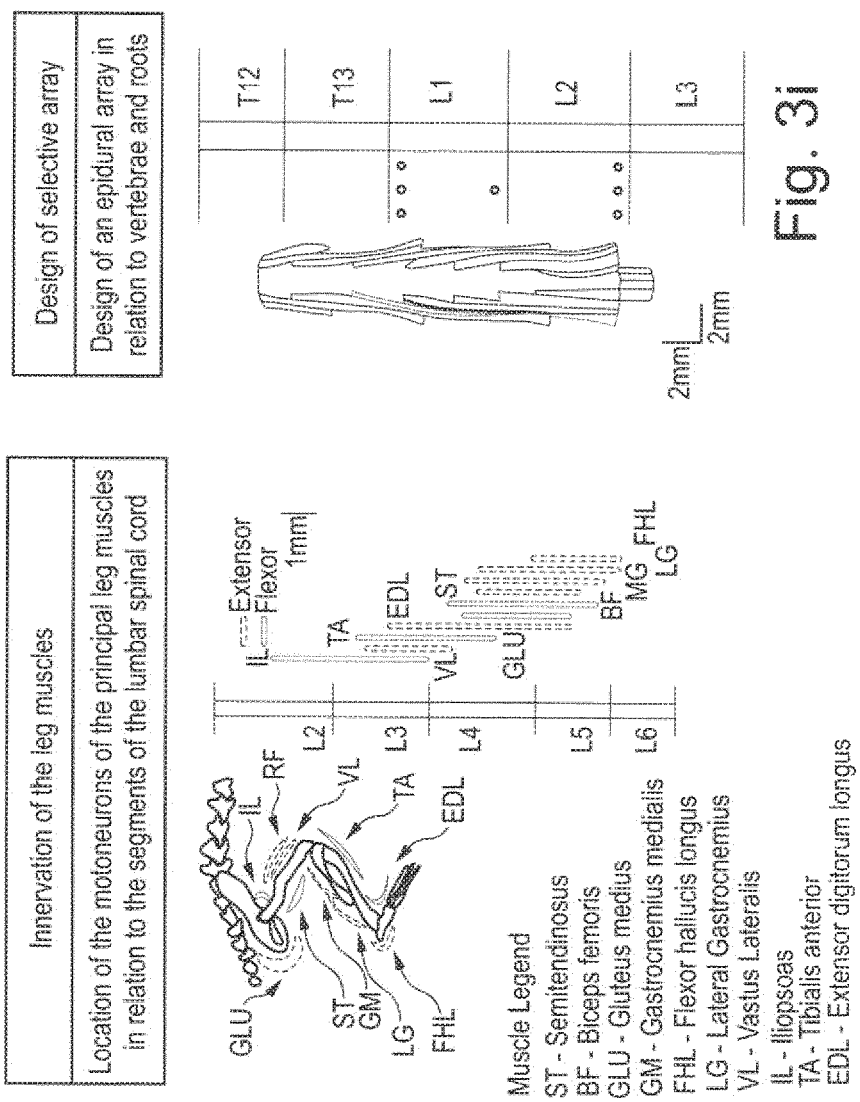
Fig. 3k
Fig. 3i
Fig. 3h

SYSTEM FOR PLANNING AND/OR PROVIDING NEUROSTIMULATION FOR A PATIENT

CROSS-REFERENCE TO RELATED APPLICATIONS

The present application is a U.S. National Phase of International Patent Application Serial No. PCT/EP2018/082946 entitled "A SYSTEM FOR PLANNING AND/OR PROVIDING NEUROSTIMULATION FOR A PATIENT," filed on Nov. 29, 2018. International Patent Application Serial No. PCT/EP2018/082946 claims priority to European Patent Application No. 17205362.1 filed on Dec. 5, 2017. The entire contents of each of the above-referenced applications are hereby incorporated by reference for all purposes.

TECHNICAL FIELD

The present invention relates to a system for planning and/or providing neurostimulation for a patient.

BACKGROUND AND SUMMARY

Decades of research in physiology have demonstrated that the mammalian spinal cord embeds sensorimotor circuits that produce movement primitives (cf. Bizzi, E., et al., *Modular organization of motor behavior in the frog's spinal cord. Trends in neurosciences* 18, 442-446 (1995); Levine, A. J. et al. *Identification of a cellular node for motor control pathways. Nature neuroscience* 17, 586-593, (2014)). These circuits process sensory information arising from the moving limbs and descending inputs originating from various brain regions in order to produce adaptive motor behaviours.

A spinal cord injury (SCI) interrupts the communication between the spinal cord and supraspinal centres, depriving these sensorimotor circuits from the excitatory and modulatory drives necessary to produce movement.

A series of studies in animal models and humans showed that electrical neuromodulation of the lumbar spinal cord using epidural electrical stimulation (EES) is capable of (re-)activating these circuits. For example, EES has restored coordinated locomotion in animal models of SCI, and isolated leg movements in individuals with motor paralysis (cf. van den Brand R, et al., *Restoring Voluntary Control of Locomotion after Paralyzing Spinal Cord Injury. Science* 336, 1182-1185 (2012); Angeli C A, et al., *Altering spinal cord excitability enables voluntary movements after chronic complete paralysis in humans. Brain: a journal of neurology* 137, 1394-1409 (2014); Harkema S, et al., *Effect of epidural stimulation of the lumbosacral spinal cord on voluntary movement, standing, and assisted stepping after motor complete paraplegia: a case study. The Lancet* 377, 1938-1947; Danner S M, et al., *Human spinal locomotor control is based on flexibly organized burst generators. Brain: a journal of neurology* 138, 577-588 (2015); Courtine G, et al., *Transformation of nonfunctional spinal circuits into functional states after the loss of brain input. Nature neuroscience* 12, 1333-1342, (2009); Capogrosso M, et al., *A brain-spine interface alleviating gait deficits after spinal cord injury in primates. Nature* 539, 284-288, (2016)).

Computational models (cf. Capogrosso M, et al., *A computational model for epidural electrical stimulation of spinal sensorimotor circuits. The Journal of neuroscience: the official journal of the Society for Neuroscience* 33, 19326-19340 (2013); Moraud E M, et al., *Mechanisms Underlying the Neuromodulation of Spinal Circuits for Correcting Gait and Balance Deficits after Spinal Cord Injury. Neuron* 89, 814-828 (2016); Rattay F, et al., *Epidural electrical stimulation of posterior structures of the human lumbosacral cord: 2. quantitative analysis by computer modeling. Spinal cord* 38, 473-489 (2000)) and experimental studies (cf. Gerasimenko Y, et al., *Program No. 447.445* (Soc. Neurosci. Abstr.); Minassian K, et al., *Human lumbar cord circuitries can be activated by extrinsic tonic input to generate locomotor-like activity. Human Movement Science* 26, 275-295 (2007)) have provided evidence suggesting that EES recruits large-diameter sensory afferents, especially proprioceptive circuits (cf. Moraud E M, et al., *Mechanisms Underlying the Neuromodulation of Spinal Circuits for Correcting Gait and Balance Deficits after Spinal Cord Injury. Neuron* 89, 814-828, (2016)).

Consequently, the stimulation leads to the activation of motoneurons through mono- and polysynaptic proprioceptive circuits, as well as increases the general excitability of the lumbar spinal cord. In addition, the natural modulation of proprioceptive circuits during movement execution gates the effects of EES towards functionally relevant spinal pathways. Concretely, due to phase-dependent modulation of proprioceptive circuits, the effects of stimulation are restricted to specific ensembles of leg motoneurons that are coherent with the phase of the movement (cf. Moraud E M, et al., *Mechanisms Underlying the Neuromodulation of Spinal Circuits for Correcting Gait and Balance Deficits after Spinal Cord Injury. Neuron* 89, 814-828 (2016)).

Moreover, since EES engages motoneurons through trans-synaptic mechanisms, residual inputs from supraspinal centres are also capable of gating the effects of EES towards specific circuits or increasing the excitability of the motoneuron pools (and thus their responsiveness to EES) in order to mediate voluntary modulation of leg movements (cf. van den Brand R, et al., Restoring Voluntary Control of Locomotion after Paralyzing Spinal Cord Injury. Science 336, 1182-1185 (2012); Angeli C A, et al., Altering spinal cord excitability enables voluntary movements after chronic complete paralysis in humans. Brain: a journal of neurology 137, 1394-1409 (2014); Harkema, S, et al. Effect of epidural stimulation of the lumbosacral spinal cord on voluntary movement, standing, and assisted stepping after motor complete paraplegia: a case study. The Lancet 377, 1938-1947).

This conceptual framework was exploited to design a neuromodulation strategy that targets specific ensembles of proprioceptive afferents associated with flexion and extension of both legs (cf. Bizzi E, et al., *Modular organization of motor behavior in the frog's spinal cord. Trends in neurosciences* 18, 442-446 (1995); Levine A J, et al. *Identification of a cellular node for motor control pathways. Nature neuroscience* 17, 586-593 (2014)).

This strategy, termed spatiotemporal neuromodulation, consists of delivering EES bursts through targeted electrode configurations with a temporal structure that reproduces the natural activation of leg motoneurons during locomotion. This spatiotemporal neuromodulation therapy reversed leg paralysis in both rodent and primate models of SCI (cf. Capogrosso M, et al., *A brain-spine interface alleviating gait deficits after spinal cord injury in primates. Nature* 539, 284-288, (2016); Wenger N et al., *Spatiotemporal neuromodulation therapies engaging muscle synergies improve motor control after spinal cord injury. Nat Med* 22, 138-145 (2016)).

This conceptual framework is applicable to develop spatiotemporal neuromodulation therapies for enabling leg motor control in humans with SCI.

Generally speaking, known stimulation systems use either Central Nerve System (CNS) stimulation, especially Epidural Electrical Stimulation (EES), or Peripheral Nerve System (PNS) Stimulation, especially Functional Electrical Stimulation (FES).

Epidural Electrical Stimulation (EES) is known to restore motor control in animal and human models and has more particularly been shown to restore locomotion after spinal cord injury by artificially activating the neural networks responsible for locomotion below the spinal cord lesion (cf. Capogrosso M et al., *A Computational Model for Epidural Electrical Stimulation of Spinal Sensorimotor Circuits*, Journal of Neuroscience 4 Dec. 2013, 33 (49) 19326-19340; Courtine G, et al., *Transformation of nonfunctional spinal circuits into functional states after the loss of brain input*, Nat Neurosci. 2009 October; 12(10): 1333-1342; Moraud E M, et al, *Mechanisms Underlying the Neuromodulation of Spinal Circuits for Correcting Gait and Balance Deficits after Spinal Cord Injury*, Neuron Volume 89, Issue 4, p 814-828, 17 Feb. 2016). EES does not directly stimulate motor-neurons but the afferent sensory neurons prior to entering into the spinal cord. In this way, the spinal networks responsible for locomotion are recruited indirectly via those afferents, restoring globally the locomotion movement by activating the required muscle synergies. The produced movement is functional; however, due to relatively poor selectivity (network activation instead of selective targeting of key muscles) the controllability is low and the imprecisions hinder fluidity and full functionality in the potential space of the movement.

Peripheral Nerve System (PNS) Stimulation systems used to date in the clinic are known as Functional Electrical Stimulation (FES) that provides electrical stimulation to target muscles with surface electrodes, either directly through stimulation of their motorfibers (neuro-muscular stimulation), or through a limited set reflexes (practically limited to the withdrawal reflex) or by transcutaneously stimulating the peripheral nerves. The resulting muscle fatigue has rendered FES unsuitable for use in daily life. Furthermore, successes have remained limited through cumbersome setups when using surface muscle stimulation, unmet needs in terms of selectivity (when using transcutaneous nerve stimulation) and a lack of stability (impossible to reproduce exact electrode placement on a daily basis when stimulating muscles, moving electrodes due to clothes, sweating).

US 2016/030750 A1 discloses a computer implemented system and method facilitates the generation, sharing and refinement of volumes to stimulate anatomical tissue, such as spinal cord stimulation. The computer system analyses the volumes as well. More specifically, a computer implemented system and method facilitates a cycle of generation, sharing, and refinement of volumes related to stimulation of anatomical tissue, such as brain or spinal cord stimulation. Such volumes can include target stimulation volumes, side effect volumes, and volumes of estimated activation. A computer system and method also facilitates analysis of groups of volumes, including analysis of differences and/or commonalities between different groups of volumes.

US 2016/001096 A1 describes methods and systems that use multiple tharepeutic modalities to cause deep or superficial deep-brain stimulation. Methods for treatment of clinical conditions and physiological impacts are described, as well as methods for Guided Feedback control of non-invasive deep brain or superficial neuromodulator, as well as the non-invasive neuromodulation of the spinal cord by ultrasound energy.

EP 2 810 689 A1 and EP 2 810 690 A1 describe a system for planning and providing a therapy for Deep Brain neural applications, especially neurostimulation and/or neurorecording with at least one lead with a plurality of electrodes. The invention concerns a method for focusing the stimulation field provided by an active contact of a lead.

US 2015/066111 A1 discloses a tool for assisting in the planning or performing of electrical neuromodulation of a patient's spinal cord by calculating a volume of activation, registering electrodes and their position.

Current systems for neuromodulation in the field of the treatment of spinal cord injuries (SCI), for example after trauma or stroke or illness, have to match each input signal to a specific reaction of the patient. This can be quite time-consuming and also exhaustive for the patient to be treated and also for the physician and medical support staff.

To further reap the therapeutic benefits of phasic EES, it may be possible to improve the manner in which phasic EES is calibrated. Currently, the tuning of EES parameters (frequency, amplitude, pulse width, and timing), is largely performed empirically. These parameters are manually adjusted over the long-lasting tuning periods of experimental sessions to obtain a locomotion pattern that most closely resembles the healthy one based on visual inspection of experimenters. This approach leads to extensive, time consuming testing, resulting in a sub-optimal selection of the stimulation parameters, and, thus, to fluctuating therapeutic outcomes. This time-consuming process is due to an unfortunate lack of established techniques to select EES parameters for the improvement of motor control. Data-driven rapid, automatic and systematic approach to estimate the EES parameters would increase therapeutic outcomes while reducing variability, errors and invested time and effort of experimenters and subjects.

This object is solved according to the present invention by a system and method for planning and/or providing neurostimulation for a patient with the features of claims 1 and 13.

Accordingly, a system is provided for planning and/or providing neurostimulation for a patient, comprising a pathological spinal cord map storage module for storing at least one pathological spinal cord map describing the activation of the spinal cord of a patient, a healthy spinal cord map storage module for storing at least one reference map describing physiological activation of the spinal cord of at least one healthy subject, an analysis module configured and arranged such that the pathological spinal cord map and the reference map can be compared and/or analyzed automatically such that a deviation map is created, the deviation map describing the difference between the pathological spinal cord map and the reference map, and a compensation module which is configured and arranged to calculate on the basis of the deviation map a neurostimulation protocol for compensating the activation difference between the pathological spinal cord map and the reference map.

The invention is based on the basic idea that pathological activation data describing the activation of a pathological spinal cord, i.e. from a patient with a spinal cord injury are compared with activation data of a healthy spinal cord data set.

Such data sets, either pathological or healthy may be collected into a so-called spinal cord map. Such maps or so-called functional maps describe the activation of the spinal cord in connection with specific activities or movements such as a gait cycle. By comparing a pathological spinal cord map and a healthy spinal cord map deviation may be found. Such deviation may be put into a so-called deviation map, which is more or less a collection of data describing the difference and activation in connection with specific activities such as movements between pathological spinal cord functionality and healthy spinal cord functionality. This deviation map then can be used by a compensation module, which uses the identified differences to calculate a neurostimulation protocol, which is needed to compensate the differences. In particular, the completely or partially not activated areas for specific movements are identified by means of the pathological spinal cord map in comparison to the healthy spinal cord map and by adding the difference or filling the gap with the neurostimulation protocol this deviation is compensated or equalized. Moreover, the spinal cord map comprises information about the α-motoneurons activation of the spinal cord. For example, activities or movements of the human body like locomotion are a basic motor activity that requires the coordination of many limb and trunk muscles. Muscle activity is a reflection of the α-motoneurons firing on segments of the spinal cord. So, the information about the α-motoneurons activation of the spinal cord can be used to describe very specifically the activation level of the spinal cord, especially in a situation after spinal cord injury (SCI).

The invention can also be used in the context of neuromodulation, especially neurostimulation, where the electrical stimulation parameters defining the stimulation for the subject to be treated can vary cyclically over time in a pre-programmed manner, i.e. one cycle with pre-defined timings for the various stimulation patterns is repeated over and over again.

Such neuromodulation approaches may cover (but are not limited to) invasive or non-invasive or mixed approaches. They may be based on neurostimulation only. Also, pharmacological approaches or the like shall be covered and understood by the term neuromodulation. Neurostimulation may be applied epidurally and/or subdurally and/or transcutaneously or in another suitable manner.

The use of pre-programmed temporal stimulation pattern data together with the use of pre-programmed spatial stimulation pattern data allow a stimulation at the correct place at the correct time to facilitate, enable or trigger the intended action of the subject. Such an action can be movement of extremities like feet and/or legs and/or arms, contraction and/or relaxation and/or any movement of muscles in connection with movement of the subject or cardiovascular functions of the subject, e.g. blood pressure control and/or blood circulation support and/or blood circulation control. Such an approach can be characterized as open-loop phasic stimulation. Basically, it forms a way to stimulate phasically the nervous system, especially the spinal cord of a subject or patient without the need for complex and/or complicated feedback systems. It can easily be implemented to promote locomotion, cyclical activity with physical training devices and reduce orthostatic hypotension, after nervous system impairments such as spinal cord injury. So it is possible to improve a neuromodulation system, e.g. in the field of improving recovery after neurological disorders like spinal cord injury (SCI), for example after trauma or stroke or illness, especially in that neuromodulation and/or neurostimulation can be provided in almost any environment and in daily life, adapted to the patient's needs and providing the needed assistance in training and daily life for the patient, also adjusted to the progress of the rehabilitation of the patient.

Furthermore, the information about the α-motoneurons activation of the spinal cord may be a calculation by means of an activation function as weighted sum of the EMGs of segments of the spinal cord, using myotomal maps as weights. For example, recordings of muscle activity (EMG) may be used to construct maps of spinal α-motoneurons activity by adding up the contributions of each muscle to the total activity to of each spinal segment, referred as "spinal maps". Spinal maps may be computed independently for both legs in case of for example movement of the legs like movements within a gait cycle. Generally speaking, also other extremities may be subject to such kind of maps. Myotomal maps may be used to determine the approximate rostro-caudal location of α-motoneurons pools in the subject's spinal cord and to map the recorded patterns of muscle activity. Such spinal maps may provide information regarding location, duration and intensity of α-motoneurons activation during any kind of movement, for example walking. In particular an average map over a movement cycle like a gait cycle may be computed to extract the average activity and then used to create a spinal cord map (either pathological or healthy spinal cord map).

Furthermore, the compensation module may be configured and arranged such that the neurostimulation protocol may be calculated such that the neurostimulation protocol may be superimposed on the pathological spinal cord map to replicate the reference map. This way of procedure uses the fact that by identifying the missing activation areas may be identified, where with adding and/or inducing activity by means of neurostimulation the missing activation may be compensated.

In particular, the compensation module may be configured and arranged such that the neurostimulation protocol is calculated such that the application of the neurostimulation protocol results in minimizing the difference between the pathological spinal cord map with the reference map.

The pathological spinal cord map and the reference map comprise information about a movement, especially a sequence of movements like e.g. a gait cycle. General speaking, also other movements like moving arms, climbing stairs, sit to stand, stand to sit, standing up, lying down or standing still may be subject to a specific pathological and/or healthy spinal cord map.

The compensation module may be configured and arranged such that related to the movement the pathological spinal cord map and/or the reference map can be segmented for calculation of the compensation. By segmentation of the movement and the related activation levels specific stages of the movement may be identified and addressed. By this, also specific muscles to be stimulated may be identified and addressed, which is for example the case during a gait cycle where specific activations of muscles are needed.

For example the legs and feet of a patient may be addressed for a gait cycle/walking such that at least
  in a first step right extension and left flexion is addressed,
  in a second step right propulsion is addressed,
  in a third step left extension and right flexion is addressed,
  in a fourth step left propulsion is addressed.

The compensation module may be further configured and arranged such that from the segmented pathological spinal cord map and the segmented the reference map the segments with the highest deviation are identified to create a distance matrix for the compensation. As many parameters are interrelated with each other, the description of this interrelation by means of a distance matrix is beneficial and advantageous.

Moreover, the system may comprise a stimulation related basic data storage module for storing stimulation related basic data defining parameters of a neurostimulation system for treating a patient, the stimulation related basic data storage module comprising at least one set of stimulation related basic data. The stimulation related basic data may be data that describe the stimulation in greater detail, in particular which kind of stimulation, which elements used for the stimulation and also the characteristics of a patient receiving the stimulation is present and/or used. Thus, the stimulation related basic data might define parameters of a neurostimulation system for treating a patient.

Furthermore, the system may comprise a stimulation related response data storage module for storing stimulation related response data of neurostimulation provided to the patient, the stimulation related response data storage module comprising at least one set of stimulation related response data including activation of the spinal cord as response to the stimulation and a stimulation related response data storage module for storing stimulation related response data of neurostimulation provided to the patient, the stimulation related response data storage module comprising at least one set of stimulation related response data including activation of the spinal cord as response to the stimulation. The stimulation related response data may describe what kind of response is received in connection with the stimulation. In particular, these kinds of data describe results of any kind triggered and received as response by the provided stimulation. Such stimulation related response data may include (but are not limited to) data describing activation of the spinal cord as response to the stimulation or specific movements and/or reactions of the patient induced by the neurostimulation. The stimulation related response data may inter alia comprise data of the activation of the spinal cord as response to the stimulation.

Additionally, the system may comprise a transfer data storage module for storing the transfer data, wherein the transfer data comprise artificial response data and/or link data and/or translation data, which link and/or translate at least partially the stimulation related basic data and the stimulation related response data with each other, the transfer data storage module comprising at least one set of transfer data and a mapping module configured and arranged such that based on the stimulation related basic data and stimulation related response data and the transfer data a digital characteristic map is generated and/or stored, which describes the interrelation between the stimulation related basic data and the stimulation related response data and the transfer data. The transfer data may be building a bridge between the stimulation related basic data and the stimulation related response data. There may be linked data and/or translation data or a deficient response data, which may fill gaps, where no direct link between an input and an output is given. In particular artificial response data might be for example but not limited to extrapolation data or calculated data. The transfer data may comprise artificial response data and/or link data and/or translation data, which link and/or translate at least partially the stimulation related basic data and the stimulation related response data with each other.

The system may comprise a stimulation related response data input module and the system may be configured and arranged such that an inverse control may be provided by inputting stimulation related response data via the stimulation related response data input module and the system may further comprise a selection module, which is configured and arranged such that based on the digital characteristic map and the deviation map suitable stimulation related basic data are selected. By an inverse control and selection of the muscles to be stimulated, i.e. defining the stimulation output and then selecting the necessary stimulation input thereto, a fast and convenient way of programming the neurostimulation system may be provided.

Moreover, the system may comprise a neuromodulation settings generation module, which is configured and arranged to translate the digital characteristic map and the deviation map into neuromodulation parameter settings for a neuromodulation treatment of a subject.

Furthermore, the present invention relates to a method for planning and/or providing neurostimulation for a patient with the features of claim 13.

Accordingly, a method is provided for planning and/or providing neurostimulation for a patient, comprising at least the following steps:

using at least one pathological spinal cord map describing the activation of the spinal cord of a patient, using at least one reference map describing physiological activation of the spinal cord of at least one healthy subject, comparing and/or analyzing the pathological spinal cord map and the reference map to create a deviation map, wherein the deviation map describing the difference between the pathological spinal cord map and the reference map, and calculating on the basis of the deviation map a neurostimulation protocol for compensating the activation difference between the pathological spinal cord map and the reference map.

Furthermore, the method may be completely done in-vitro without connection to a patient.

In particular, the method may be performed offline on the basis of separately obtained patient data. No connection to the patient is necessary to perform the method for planning and/or providing neurostimulation for a patient.

Explicitly disclosed is a method for planning and/or providing neurostimulation for a patient comprising the above steps obtained and performed with the system for planning and/or providing a neurostimulation for a patient.

The system and the method may be used to restore locomotion or any other movement.

Locomotion is a basic motor activity that requires the coordination of many limb and trunk muscles. Muscle activation is a reflection of $\alpha$-motoneurons firing on the spinal cord. The activation of $\alpha$-motoneurons during locomotor tasks seems to occur in bursts at discrete times, which depend on the speed and on limb loading.

The goal of the proposed algorithm is to design a subject-dependent spinal cord stimulation strategy based on $\alpha$-motoneuron activation to restore locomotor tasks in subjects with motor impairments. Spinal cord stimulation can modulate the $\alpha$-motoneuron activation of the subject with impairment and therefore replicate the healthy activation during locomotion. A stimulation strategy is composed of a sequence of protocols of stimulation, where each protocol involves several stimulation parameters (frequency, amplitude, pulse width, onset, and duration). The design is composed of two separate steps. Firstly, activation of the spinal $\alpha$-motoneurons is explored by the application of different protocols of stimulation. To this end, each stimulation parameter is modulated and the effect on the spinal $\alpha$-motoneurons is observed. This process provides a spectrum of all activations induced by each stimulation protocol. Secondly, based on the stimulation-induced spinal activation dataset, the algorithm elaborates the optimal stimulation strategy. Selection of the optimal stimulation protocols is based on the difference between healthy and injured spatiotemporal rostro-caudal activations of the spinal cord during specific task execution.

A spinal map is the representation of the muscle activity, as a reflection of the $\alpha$-motoneurons firing on the spinal segments. Therefore, firstly, the muscle activities are recorded and processed to extract the envelope of the EMG signals. Secondly, myotomal maps are used to determine the approximate rostro-caudal location of α-motoneurons pools in the subject's spinal cord. The assumption is that such processed EMG provides an indirect measure of the net firing of motoneurons of that muscle in the spinal cord. Finally, an activation function is used to compute the activations of the spinal segments as weighted sums of the EMGs, using the myotomal maps as weights. Furthermore, spinal maps are averaged over the locomotive task cycles (i.e. from foot strike to the following foot strike of the same leg in the gait cycle) to observe the average activity of the α-motoneurons.

A reference spinal map (RSM) is computed from the locomotion of healthy subjects and the injured spinal map (ISM) is extracted by the locomotion of the impaired subject. The numerical difference between RSM and ISM provides a differential map (DSM), which shows the missing activation focuses on the subject's spinal cord. The DSM represents the stimulation strategy to apply using EES.

The principles of the algorithm are to replicate the DSM of the ipsilateral leg and to not activate the α-motoneurons pools of the contralateral leg. The spectrum of the stimulation-induced activation is used to mimic each sample of the DSM. A fitting rate is assigned to each protocol based on the ability of the induced activation to mimic the samples of the DSM. In parallel, the contralateral activation generated by the stimulation protocol is used to assign a negative rate to it. Finally, for each DSM sample, a combination of the two rates is used to select the stimulation protocol whose activation better cope with the requirements.

The described algorithm is extremely versatile and translatable among diseases or injuries that cause locomotor disorders, such as spinal cord injury or Parkinson disease. Moreover, it substantially enhances the EES-based therapies and, thus, leads to improved locomotion. It provides a direct feedback on the efficacy of the stimulation and an indicator for the optimal electrode configuration. Moreover, it can be thought of as a first step towards a spinal cord neuroprosthesis. It is focused on the exploration and exploitation of the stimulation arrays by identifying the most effective stimulation protocols.

BRIEF DESCRIPTION OF THE FIGURES

Further details and advantages of the present invention shall now be disclosed in connection with the drawings.

It is shown in

FIG. 3a-k several details of the anatomical structures to be stimulated and anatomical structures of interest;

DETAILED DESCRIPTION

Figure 1:
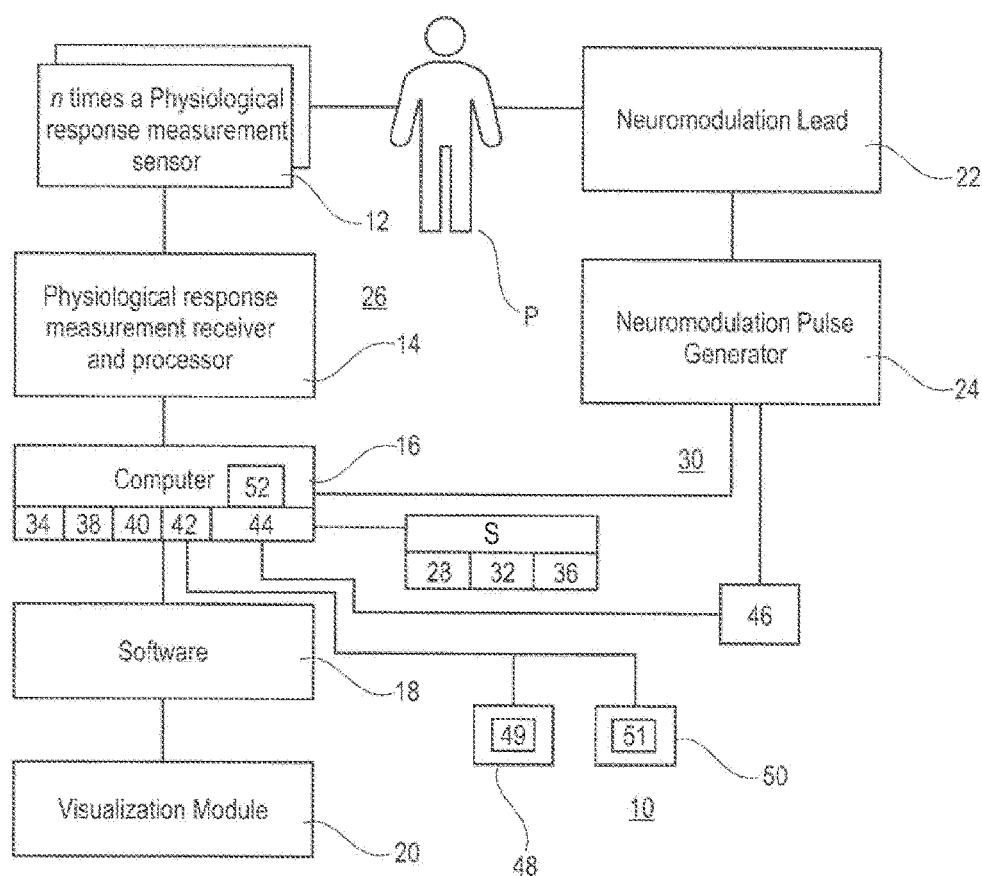
FIG. 1 a schematical overview of a possible embodiment for a system for planning and/or providing neuromodulation.

FIG. 1 shows as schematical overview of a possible embodiment for a system for planning and/or providing neuromodulation, here neurostimulation according to the present invention.

The patient P is connected to the system 10.

The system 10 comprises at least:
a physiological response measurement sensor 12
a physiological response measurement receiver and processor 14
a computer 16
a software 18
a visualization module 20
a neuromodulation lead 22 and neuromodulation pulse generator 24.

The physiological response measurement sensor 12 and the physiological response measurement receiver processor 14 function as a first data input module 26 for stimulation related basic data.

The computer 16 and the software 18 are connected to a storage being part of the computer 16.

The storage S comprises a stimulation related basic data storage module 28 for storing the stimulation related basic data obtained by the first data input module 26 for stimulation related basic data.

The stimulation related basic data may comprise at least one (or more or all) selected from
electrode data, and/or
stimulation characteristic data, and/or
patient data, and/or
stimulation data, and/or
treatment application data.

In the shown embodiment, the neuromodulation lead 22, the neuromodulation pulse generator 24, the physiological response measurement sensor 12 and the physiological response measurement receiver and processor 14 form also a second data input module 30 for stimulated related response data.

The stimulation related response data are stored in a further stimulation related response data storage module 32, which is also part of the storage S.

The stimulation related response data comprise data comprise at least one (or more or all) selected from
sequence of events data, and/or
motion data, and/or
EMG (electromyography) data, and/or
afferent signal data, and/or
efferent signal data, and/or
impedance data, and/or
EEG (electroencephalograhy) data, and/or
BCI (brain control interface) data.

Moreover, the computer 16 comprises a transfer module 34.

The transfer module 34 is configured and arranged such that the stimulation related basic data received by the data input module are linked and/or translated into and/or with the response data and/or artificial response data created by the transfer module 34, wherein the data generated by the transfer module 34 are transfer data, the transfer data comprising link data and/or translation data and/or artificial response data.

The transfer module 34 may configured and arranged such that at least one kind of data selected from
- body posture data, and/or
- static and/or dynamic data, and/or
- task and/or activity data, and/or
- time and/or delay data, and/or
- rehabilitation data, and/or
- drug treatment data, and/or
- data related to the voluntariness of movement, is or are used to generate the transfer data.

Moreover, there is a transfer response data storage module for storing the transfer data, which is also part of the storage S.

Furthermore, the computer 16 comprises for creating a digital characteristic map 36 a mapping module 38.

The mapping module 38 is configured and arranged such that based on the stimulation related basic data and the stimulation related response data and the transfer data digital characteristic map 36 is generated, which describes the interrelation between the stimulation related basic data and the stimulation related response data and the transfer data.

The mapping module 38 may be configured and arranged such that the digital characteristic map 36 is generated automatically.

The system 10 may further comprise a virtual mapping module 40, which is configured and arranged to generate the digital characteristic map virtually online.

Moreover, the system 10 comprises a correlation and/or simulation module 42, which is configured and arranged to correlate on the basis of digital characteristic map by way of simulation the stimulation related basic data and the stimulation related response data and the transfer data.

The correlation and/or simulation module is configured and arranged such that from a preselected stimulation related basic data the correlating stimulation related response data are identified. Also, from a preselected stimulation related response data the correlating stimulation related basic data may be identified.

The system 10 further comprises a neuromodulation settings generation module 44, which is configured and arranged to translate the digital characteristic map into neuromodulation parameter settings for a neuromodulation treatment of a subject.

Furthermore, the neuromodulation settings generation module 44 comprises a transfer interface 46, which is configured and arranged for transferring neuromodulation parameter settings from the system to a neuromodulation device, here the Neuromodulation Pulse Generator 24.

The analysis module 42 is configured and arranged such that the digital characteristic functional map can be analyzed in connection with neurostimulation provided by the neurostimulator such that the provided neurostimulation and and its response can be analyzed on the basis of the functional map and that on the basis of this analysis an placement analysis of the placement of the electrode is provided.

The visualization module 20 is configured and arranged such that at least partially stimulation related basic data and at least partially stimulation related response data are displayed.

The visualization module 20 is configured and arranged such that stimulation related response data are visualized at least schematically with representations of muscles or muscles group receiving neurostimulation.

The system 10 comprises stimulation related response data input module 28 and that the system is configured and arranged such that an inverse control is provided by inputting stimulation related response data via the stimulation related response data input module and that system further comprises selection module, which are configured and arranged such that based on the digital characteristic map suitable stimulation related basic data are selected.

The system 10 further comprises a pathological spinal cord map storage module 48.

Also, there is a healthy spinal cord map storage module 50.

The pathological spinal cord map storage module 48 serves for storing at least one pathological spinal cord map 49 describing the activation of the spinal cord of a patient.

The healthy spinal cord map storage module 50 serves for storing at least one reference map 51 describing physiological activation of the spinal cord of at least one healthy subject.

The analysis module 42 is also configured and arranged such that the pathological spinal cord map and the reference map can be compared and/or analyzed automatically such that a deviation map is created, the deviation map describing the difference between the pathological spinal cord map and the reference map.

The system 10 also comprises a compensation module 52.

The compensation module 52 is configured and arranged to calculate on the basis of the deviation map a neurostimulation protocol for compensating the activation difference between the pathological spinal cord map and the reference map.

The above system and process may be also set up as a self-learning or machine-learning process. Especially all kind of maps may be generated in a self-learning or machine-learning process.

Figure 2:
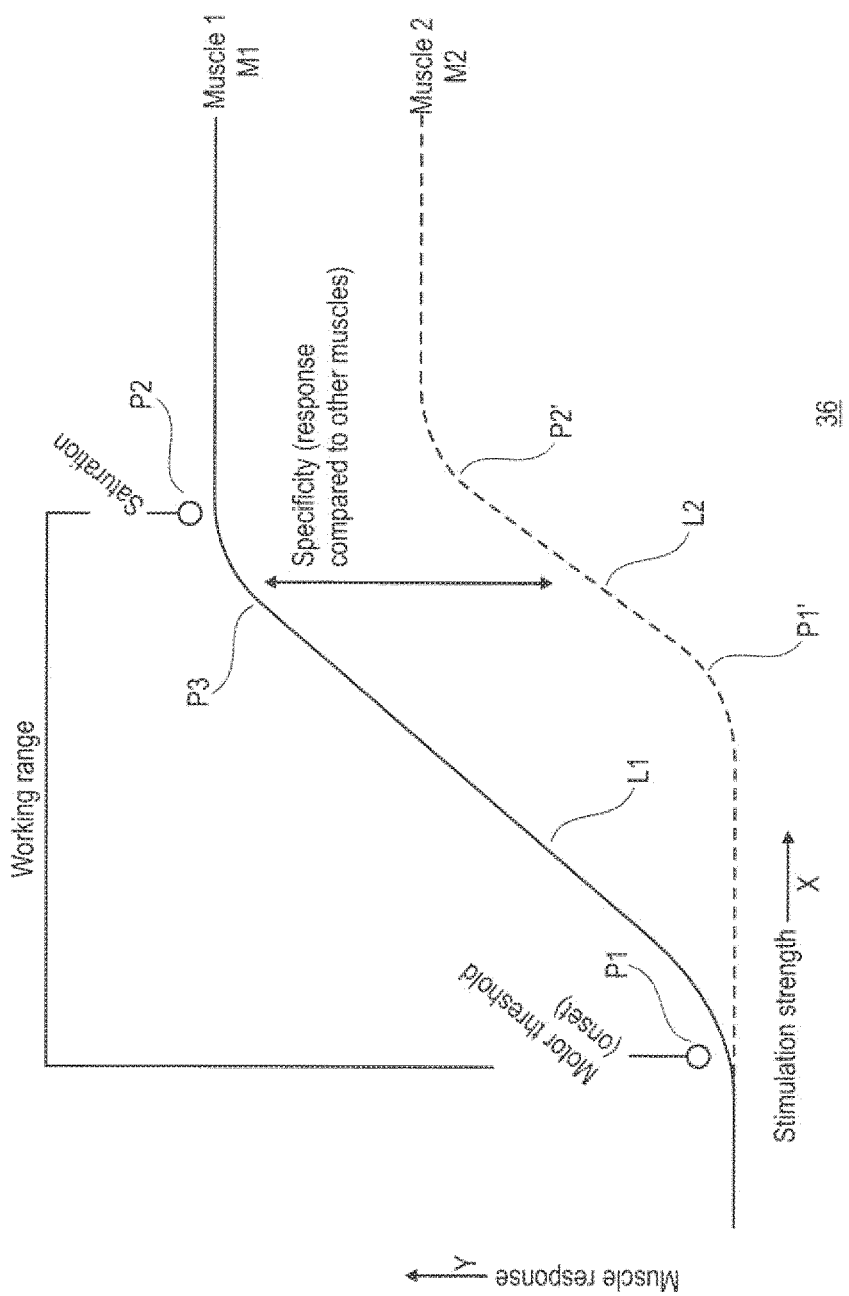
FIG. 2 a (two-dimensional/2D) part of the obtained digital characteristic map.

FIG. 2 shows in 2D a part of the obtained digital characteristic map 36, describing the interrelation between the stimulation related basic data and the stimulation related response data and the transfer data.

On the x-axis the stimulation strength is shown.

On the y-axis the muscle response is shown.

In the digital characteristic map 36, two lines L1 and L2 describing the connection between the stimulation strength (i.e. stimulation related basic data) with the muscle response (stimulation related response data), wherein the connection can be seen as kind of a transfer function (i.e. stimulation related transfer data).

The first line L1 is describing the stimulation response of a first muscle M1 and the dashed line L2 is describing the stimulation response for a second muscle M2.

As can be seen, at a point of stimulation P1 muscle M1 starts to react.

This point P1 is called motor threshold point or onset point.

At this point P1, muscle M2 shows no reaction.

Increasing the stimulation strength will result at some point in a saturation, this point being denoted as point P2, also called saturation point P2.

This point P2, being the saturation point is defining the point at which no further stimulation will receive in stronger muscle activity of muscle M1.

Thus, this point is called saturation point, as increasing the stimulation will not result in better stimulation results and muscle activity.

As can be seen, at point P1' a second muscle starts to react on the applied stimulation, however, at a lower level and with less activity. So, a specificity point P3 may be defined.

The specificity point P3 defines a point, where muscle M1 shows relatively high response, whereas the response of muscle M2, which is also stimulated by the applied stimulation shows less activity, which is still at a level that can be accepted, as it is not really relevant.

Also shown is the saturation point P2' for muscle M2.

FIG. 2 shows a part of digital characteristic map for example for a specific subset of electrodes of an electrode array that is placed in the vicinity of the spinal cord, for example to perform epidural electrical stimulation (EES). By already knowing the connection the placement of the electrodes vis-a-vis the spinal cord and the afferent sensory neurons, the necessary muscles or muscle groups needed for a specific movement can be addressed.

When generating the digital characteristic map, the user is confronted with a plurality of degrees of freedom.

Moreover, fast scans are limited by the response time of the muscles (approx. 2 s/0.5 hz).

This will lead to long mapping times for generating the digital characteristic map.

Thus, here optimization might be wanted.

This can be done by optimizing the patients specific mapping procedure, i.e. finding the optimal stimulation settings for a given task.

Therefore, the following options can be used alternatively or in combination:

By applying specific search function instead of a current step-wise approach, the time consuming step-wise approach can be avoided. Possible approaches in connection with this search function approach are particle swarm, genetic, steepest gradient, optimization algorithms.

A model fitting approach may be used. Here, a patient specific or generic model or the like may be used that predicts muscle response for a specific stimulation and uses the actual mapping to fine-tune and/or register and/or adapt this model to the individual/specific patient.

There may be a data base of patients. Here iterative/machine learning methods may be used for mappings from previous patients to suggest (patient-specific) stimulation settings, probabilistic/statistics can be used, e.g. if one use those settings, then the probability of an effective stimulation may be a certain percentage X % and the crosstalk may be another certain percentage Y %.

For the above three methods, certain quality indicators/optimization object functions may be used such as sensitivity index, cross-talk, muscle onset, muscle saturation or the like.

The above three approaches may improve the generation of the digital characteristic map (the so called mapping procedure) by:
reducing the mapping times
creating patient specific optimum results
potential reduction of the number of EMG's required, making the procedure easier and faster
theoretically one can abandon the use of EMG's at all by fine-tuning of the used motion sensors.

FIG. 3a-k show several details of the anatomical structures to be stimulated and anatomical structures of interest.

FIG. 3a-e relates to the example of Rhesus monkeys.

FIG. 3f-k relate to rodents, here Louis rats.

Figure 3C:
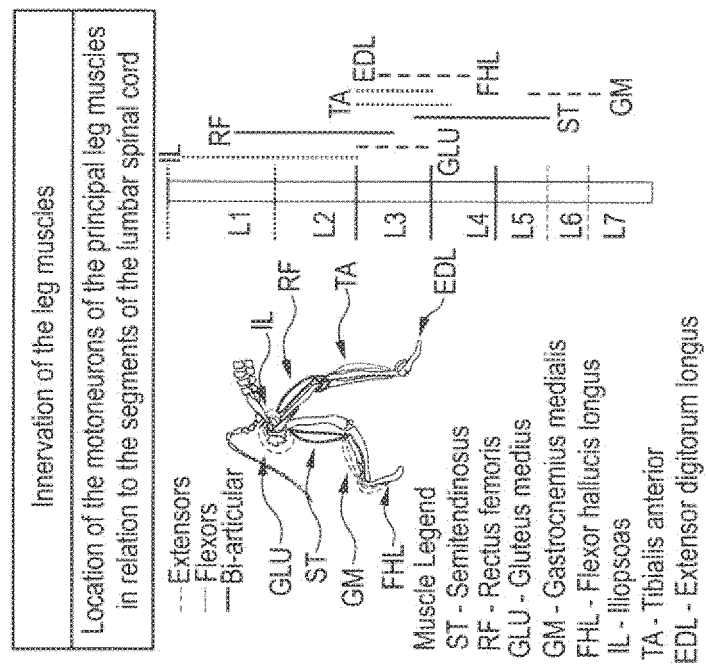
Figure 3B:
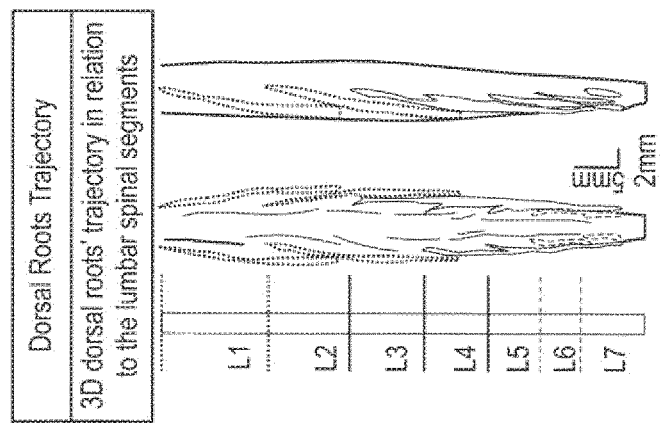
Figure 3A:
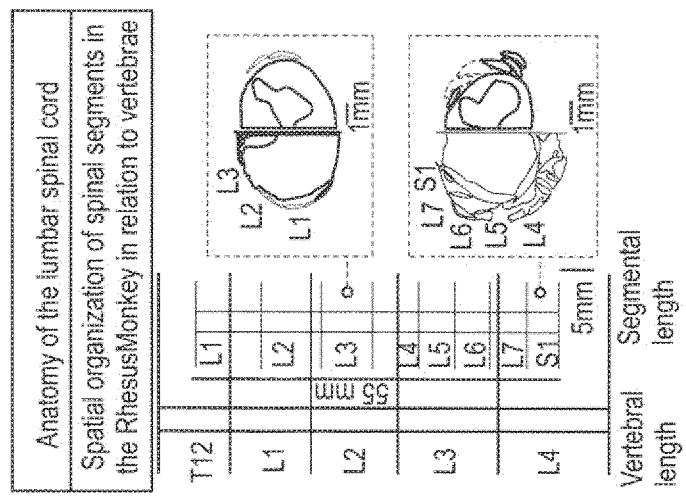

FIG. 3a shows the anatomy of the lumbar spinal cord of a Rhesus monkey to be stimulated.

Here this spatial organization of spinal segments of the Rhesus monkey in relation to the vertebrae is shown.

FIG. 3b shows the dorsal roots trajectory.

Here the 3D-dorsal roots' trajectory in relation to the lumbar spinal segment is shown.

FIG. 3c shows the innervation of leg muscles, in particular the location of the motor neurons of the principle leg muscles in relation to the segments of the lumbar spinal cord.

Shown are extensor muscles with the denotation EXT, flexor muscles with the reference sign FLEX and the articular muscles with the reference sign B.

The muscles are denoted as follows:
ST—SEMITENDINOSUS
RF—RECTUS FEMORIS
GLU—GLUTEUS MEDIUS
GM—GASTROCNEMIUS MEDIALES
FHL—FLEXOR HALLUCIS LONGUS
IL—ILIOPSOAS
TA—TIBIALIS ANTERIOR
EDL—EXTENSOR DIGITORUM LONGUS.

Figures 3D, 3E, 3F, 3G:
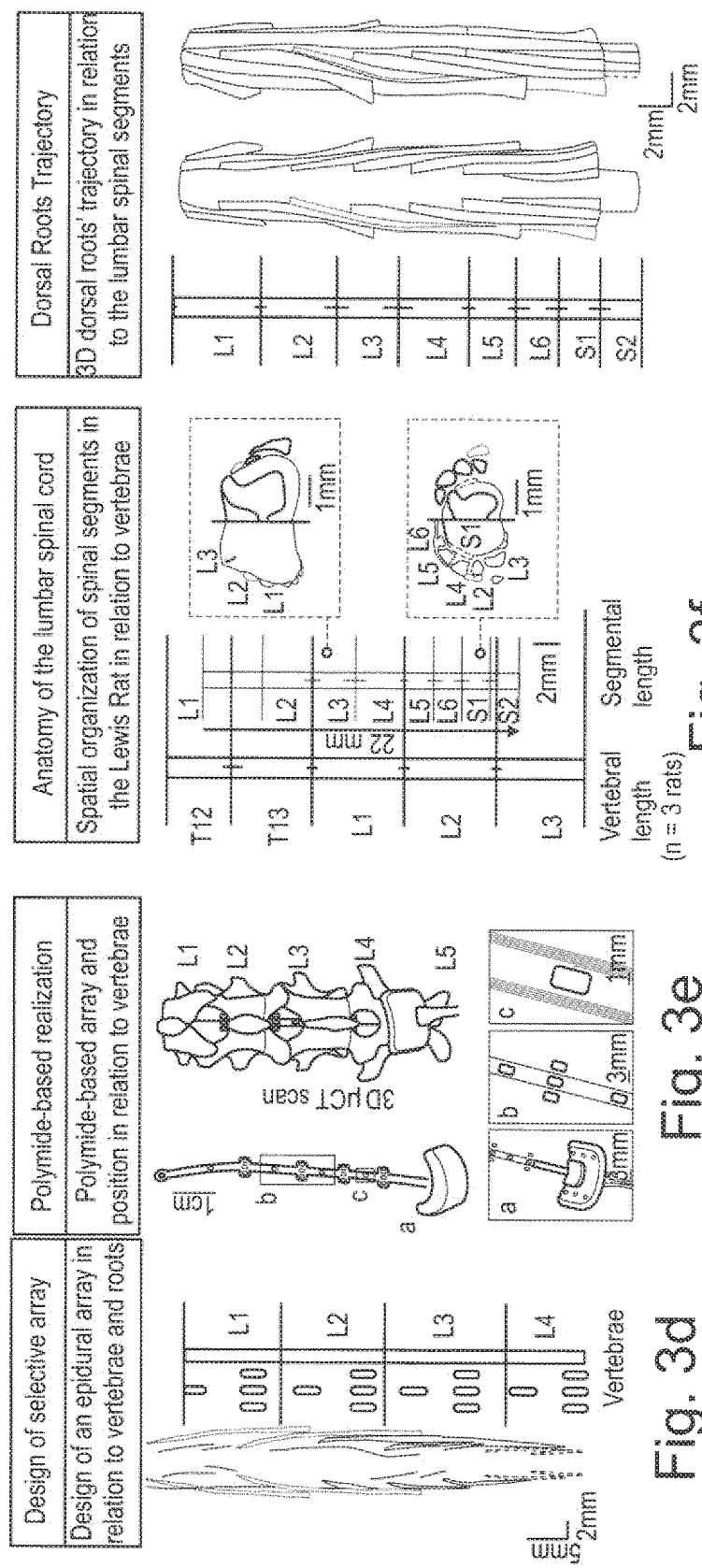

FIG. 3d shows the design of a selective array of electrodes of for example a neuromodulation lead 22.

Here, the design of an epidural array in relation to the vertebrae and roots of the spinal cord is shown.

FIG. 3e shows a polyamide-based realization.

Here, the polyamide-based array and position in relation to the vertebrae is shown.

FIG. 3f-k show respectively the corresponding drawings for rodents, here Lewis rats.

In particular, it is shown in
FIG. 3f the anatomy of the lumbar spinal cord of a rodent,
FIG. 3g the dorsal roots trajectory,
FIG. 3h the innervation of the leg muscles,
FIG. 3i the design of the selective array, and
FIG. 3k the polyamide-based realization.

Figure 4:
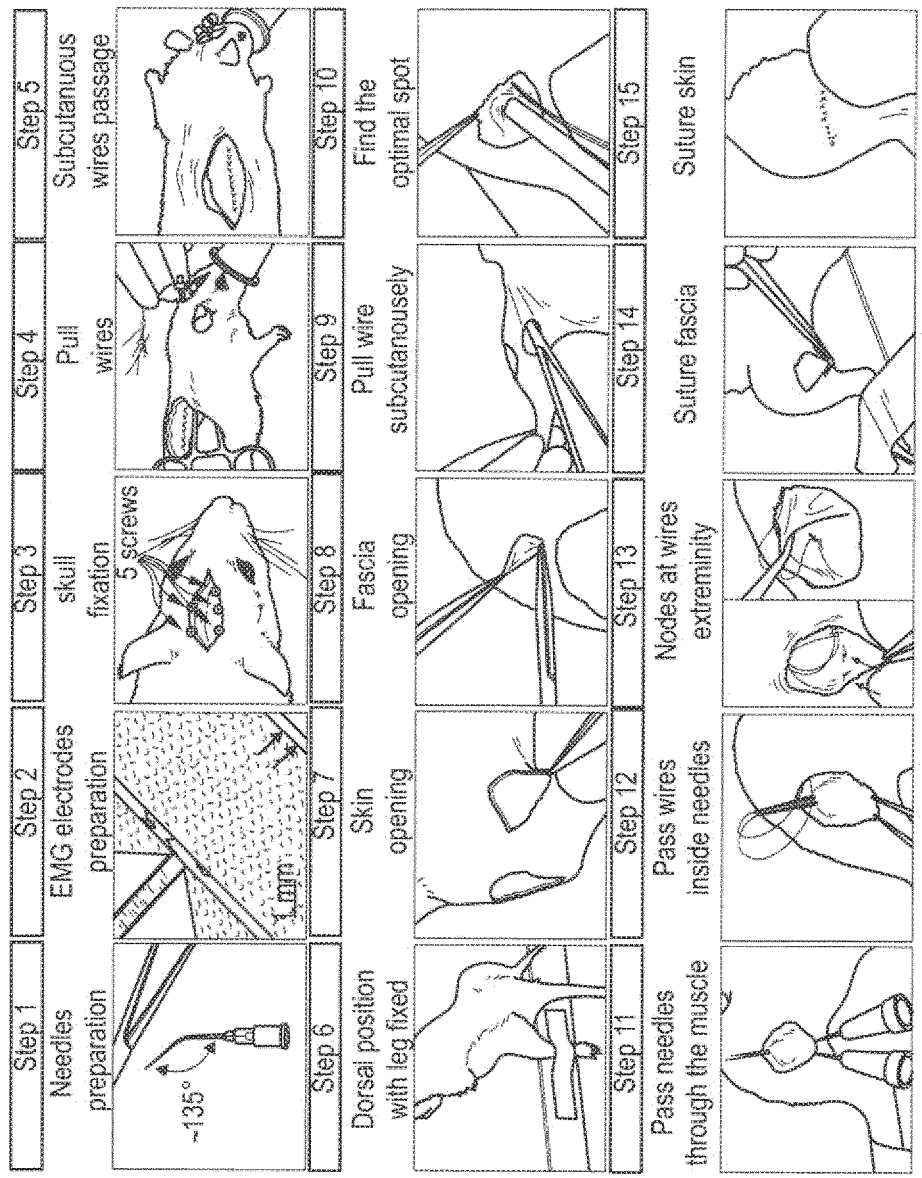
FIG. 4 the implantation procedure of a neuromodulation lead of a system according to FIG. 1, here in connection with the example of the implantation of a neuromodulation lead for a rodent (here a Lewis rat)

FIG. 4 shows the implantation procedure of the neuromodulation lead 22, here in connection with the example of the implantation of a neuromodulation lead for a rodent (here a Lewis rat).

The implantation of a neuromodulation lead for other mammals like monkeys or human beings is similar.

In step ST1 the needles are prepared.
In step ST2 the EMG electrodes are prepared.
In step ST3 a skull fixation is done.
In step ST4 the lead wires are pulled.
In step ST5 subcutaneous wire passage is prepared and provided.
In step ST6 a dorsal position with leg fixed is performed.
In step ST7 a skin opening is performed.
In step ST8 a fascia opening is performed.
In step ST9 the wires are subcutaneously pulled.
In step ST10 the optimal spot is found.
In step ST11 needles are passed through the muscles.
In step ST12 wires are passed inside the needles.
In step ST13 notes at wires extremity are provided.
In step ST14 the fascia is provided with a suture.
In step ST15 a suture to the skin is performed to close the implantation side.

Figure 5:
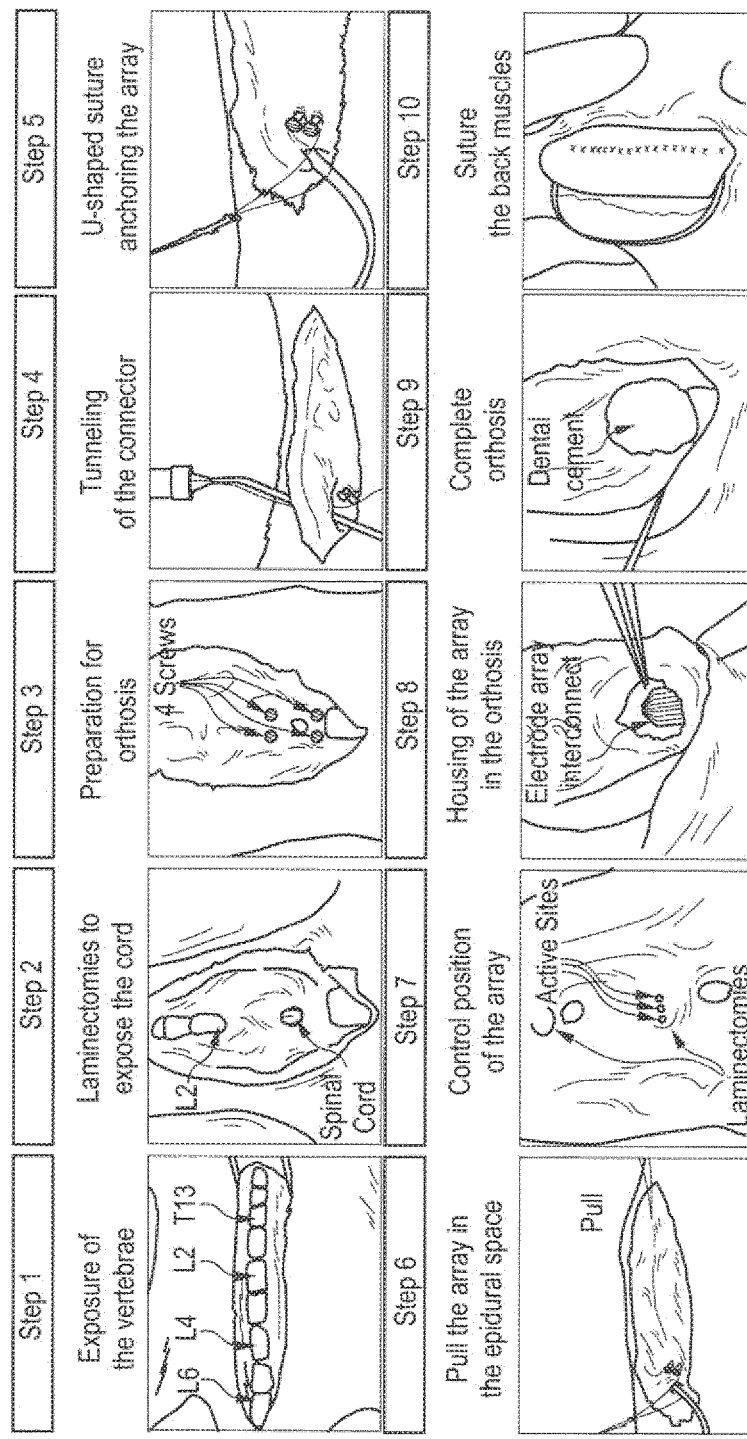
FIG. 5 further steps of implanting an electrode array to the spinal cord.

FIG. 5 shows further steps of implanting an electrode array to the spinal cord.

In step ST100 the exposure of the vertebrae is done.
In step ST110 laminectomies are done to expose the spinal cord.
In step ST120 a preparation for the orthosis is done by using 4 screws.
In step ST140 a tunneling of the connector is prepared and provided.
In step ST150 a ushape suture is provided for anchoring the electrode array of the neuromodulation lead 22.
In step ST160 the array is pulled into the epidural space.
In step ST170 a control position the array is done.

In step ST180 a housing of the array is provided in the orthosis.

In step ST190 a complete orthosis is performed by using dental cement. This orthosis is used for the rodents to support them during "walking". It is not needed for other mammals like primates (e.g. monkeys or humans).

In step ST200 a suture of the back muscles is provided to close the implantation side.

Figure 6A:
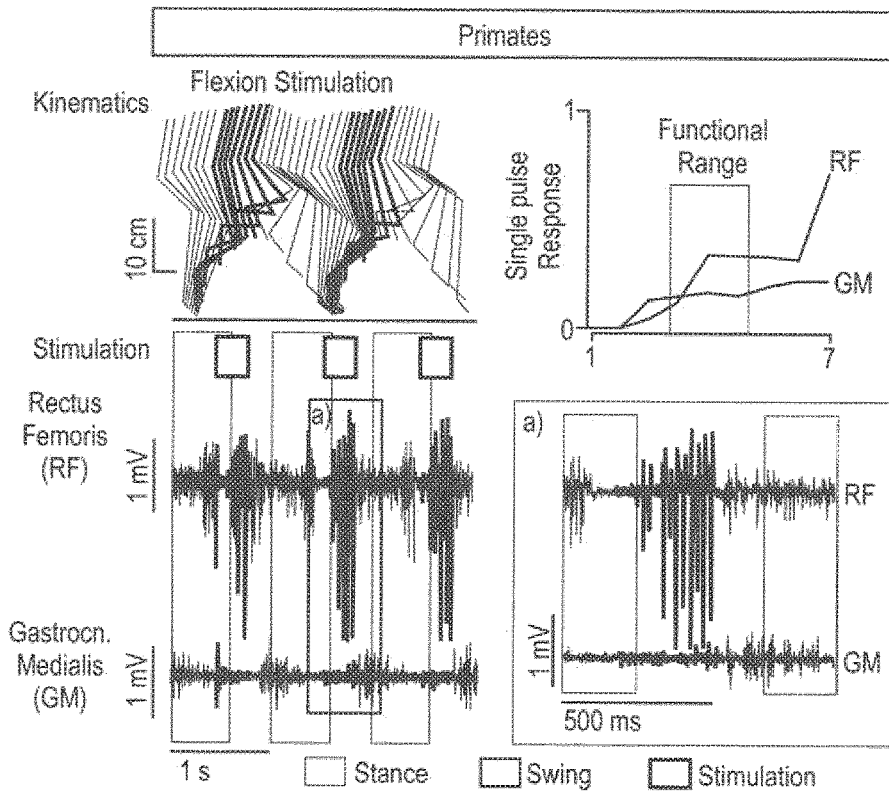
FIG. 6a the kinematics and the stimulation in the functional range on flexion stimulation for primates.
Figure 6B:
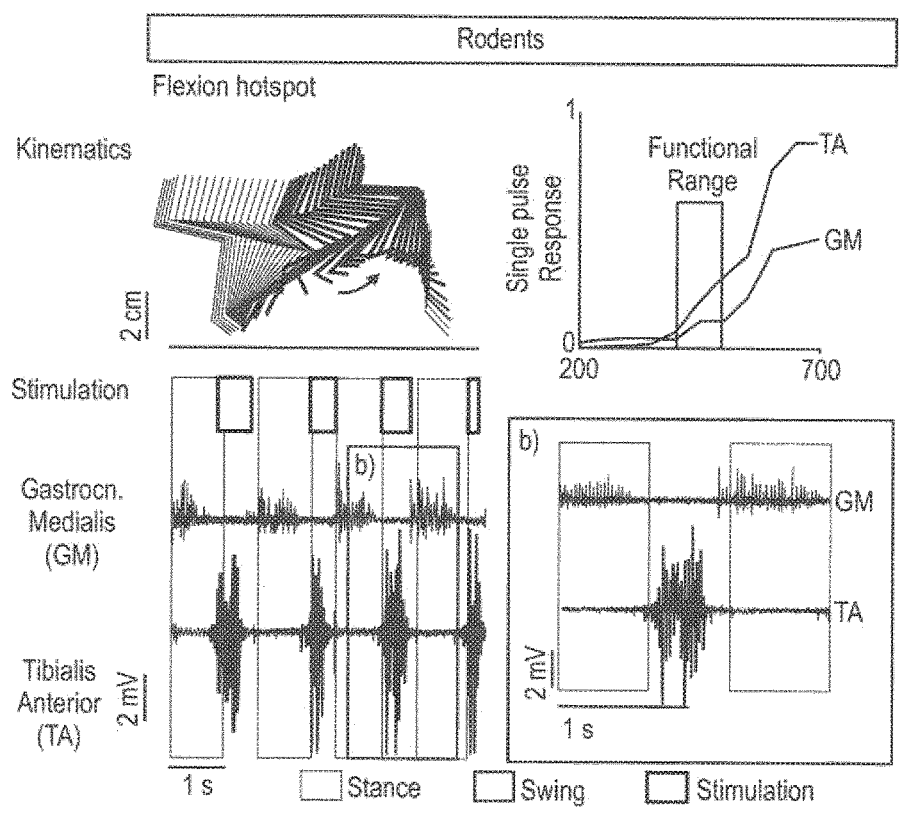
FIG. 6b the kinematics and the stimulation in the functional range on flexion stimulation for rodents.

In FIG. 6a the kinematics and the stimulation in the functional range on flexion stimulation for primates is shown. The corresponding relationship for rodents is shown in FIG. 6b.

Method of Functional Mapping

The method of functional mapping may be performed for example as follows:

Evaluation of the spatial specificity of epidural arrays is achieved by simple electrophysiological testing. A single supra-threshold current pulse of EES, applied through an electrode contact at the lumbosacral level, produces mono- and poly-synaptic electromyographic responses in some leg muscles termed spinal reflexes (FIG. 6a and FIG. 6b).

In particular, the mono-synaptic component of these responses, appearing at the lowest threshold, is related to the direct activation of the Ia afferent fibers. These fibers have excitatory synaptic connections to all the motoneurons of their homonymous muscle. Therefore, given the location of motoneuron pools in the spinal cord (cf. e.g. FIG. 3c and FIG. 3h) and which muscles are activated by single pulses (or low-frequency stimulation, e.g. 0.5-2 Hz) of epidural stimulation, it is possible to infer which roots are stimulated by each of the active sites. This procedure enables to estimate the region of the spinal cord that is preferentially targeted by a specific contact (cf. e.g. FIG. 6a and FIG. 6b).

Indeed, the specificity of epidural arrays for spatiotemporal neuromodulation is not defined by the ability to stimulate single muscles, but rather by the recruitment of specific spinal segments innervating several muscles at the same time. Some antagonist muscles, such as the tibialis anterior and gastrocnemius *medialis*, may be partially innervated by roots emerging from the same segment. However, spinal circuits and interactions with residual descending control will gate the stimulation effects towards functionally relevant muscles during the execution of a specific movement. The excitability of agonist and antagonist muscles is modulated during gait, resulting in increased functional muscle specificity during movement (cf. e.g. FIG. 6a and FIG. 6b) compared to static measurements. This provides additional robustness in the positioning of the implants. During the implantation procedure, the ability to elicit spinal reflexes in the muscles innervated by the most rostral and the most caudal spinal segments innervating leg muscles (such as the Iliopsoas and Gastrocnemius Medialis respectively) ensures a correct longitudinal placement of the array and a full coverage of the entire lumbosacral spinal cord.

Procedure

Implantation of chronic electromyographic (EMG) electrodes and epidural spinal electrode arrays in rats and primates is done as shown in FIG. 4 and FIG. 5.

For primates or humans the implantation of the neurostimulation lead is done likewise the implantation of electrode arrays for neurostimulation of the spinal cord in connection with pain treatment.

After the implantation, the following exemplary steps for Intra-operative electrophysiology and finalization of the implantation procedure for the epidural array of the neuromodulation lead 22 are performed.

The EMG electrodes are connected and the epidural array to the Real-Time electrophysiology unit.

The system 10 set up to visualize on a monitor and store 50 ms of EMG signals triggered by each stimulation pulse delivered through the epidural array.

Then, the neural stimulator with the neuromodulation pulse generator 24 and the neuromodulation lead 22 is set to current mode (voltage mode can also be used but is not preferred). The stimulation frequency may be chosen at e.g. 0.5 Hz. In general, a current range from 0 to 600 µA in rats and 0 to 5 mA in primates or humans at 200 µs pulse-width may be expected.

After this, one may proceed by stimulating the most rostral sites to verify that the Muscle Evoked Potential of the iliopsoas in response to the epidural stimulation is recruited at lower threshold than the other leg muscles. Stimulation of the most rostral lumbar segments of the spinal cord should induce isolated hip flexion movements associated to each stimulation pulse when the stimulation is applied above motor threshold.

In the next step it is continued by stimulating the most caudal sites to verify that the Muscle Evoked Potential of the Medial Gastrocnemius in both rats and primates (or another most caudally innervated muscle) in response to the epidural stimulation is recruited at lower threshold than other leg muscles. A current amplitude range from e.g. 0 to 300 µA in rats and 0 to 2 mA in primates or humans at 200 µs pulse-width for the stimulation of the caudal spinal cord may be expected. Stimulation of this region should induce isolated ankle dorsi-flexion movements associated to each stimulation pulse when the stimulation is applied above motor threshold.

Then, the longitudinal position of the array may be adjusted by e.g. sliding it under the vertebra and previous steps may be repeated until both conditions are met.

Following to this step/these steps, the medio-lateral positioning of the array is checked by verifying that stimulation of lateral sites at the same spinal level selectively recruits the muscles of the leg ipsilateral to the stimulation site at lower current levels than the muscles of the contralateral leg. The position of the array is adjusted by using the openings provided by the laminectomies at various spinal levels.

Spatial Specificity: Post-Surgical Selection of Optimal Electrode Configurations Firstly, the epidural spinal stimulation system is set up. In rats, the headplug receiving the wires from the epidural electrode array is connected to to a multichannel stimulator controlled by a computer or real-time processor (e.g. RZ2 Bioamp Processor, Tucker-Davis Technologies). In primates or humans establishing communication with an Implantable Pulse Generator (IPG) (e.g. Activa RC, Medtronic). Communication occurs via a telemetry system consisting of an antenna linked to an interface worn by the animal and placed in a custom-made jacket. This interface should be able to transmit information wirelessly (e.g. by Bluetooth) to an external computer. Such systems with real-time communication capabilities do not readily exist as commercial system but can be used as investigational devices through collaborations with biomedical companies such Medtronic.

Optionally, a video recording or motion capture system may be used to record the movements that will be induced by epidural stimulation (as described in the following point).

The spatial selectivity of the electrode array is characterized following a procedure similar to that described on connection with the verification of the Muscle Evoked Potential of muscles of interest. The stimulation is set by selecting an electrode site and send single bipolar electrical pulses (200-μs pulse width) at a frequency of 0.5 Hz. The electrode site being tested is selected as the cathode (negative polarity).

Then, the stimulation amplitude is manually increased from until a motor evoked potential is observed. A motor potential elicited by the stimulation should occur within about 3-8 ms in the rats and 5-15 ms in the primates after the stimulation pulse. Take note of the minimum intensity eliciting a motor potential as the motor threshold.

The intensity is increased until the motor responses on all muscles saturate in amplitude and take note of the saturation amplitude.

A recording of the EMGs is performed while systematically ramping up the stimulation amplitude from 0.9× the motor threshold found until the saturation amplitude found.

The above steps are repeated for each electrode of the spinal implant, until muscle responses evoked by each of the electrode contacts are recorded.

Optionally, a testing of additional multipolar electrode configurations may be performed. In the case in which leg specificity or muscle specificity is considered insufficient, multipolar configurations can be used to increase it. For example if all the electrodes on the left side of the array induce responses in both limbs, multipolar configurations may be tested with the cathode on the left side and the anode on the midline or on the right side in order to steer the activating field towards the desired limb. Likewise, if there is a lack of rostro-caudal selectivity, for example if the iliopsoas (most rostral muscle) is not specifically recruited by the most rostral electrodes, the cathode may be placed on the most rostral electrode and one or several anodes on the electrodes caudal to it.

When all recordings are completed the local procedures defined for awakening and post-sedation care will be performed.

Then, the recruitment curves and the digital characteristic are calculated and computed offline from the data obtained in the steps described above. Recruitment curves indicate the normalized level of activation of each muscle in response to single electrical pulses of increasing amplitude. The EMG activity is normalized by its maximum across all stimulation amplitudes and all stimulation sites. These recorded motor responses can also be translated into spatial maps of motoneuron pool activation, so-called spinal maps. From the recruitment curves, identify a functional range of stimulation amplitudes in which only the muscles activated at the lowest thresholds are significantly recruited. The spinal maps are computed corresponding to this functional range and use them to define the spatial specificity of each electrode configuration.

By analyzing the computed spinal maps, the electrode configuration is determined that creates the highest activation in the spinal segments responsible for flexion of the leg, especially hip flexion (L1-L2 in rats during bipedal locomotion, L1-L2 in primates) and has unilateral responses over a wide range of amplitudes. This configuration is selected to promote global flexion of the leg. Similarly, the electrode configuration is determined that creates the highest activation in the spinal segments responsible for extension of the leg, especially ankle extension (L4-L6 in rats during bipedal locomotion, L6-L7 in primates) and has unilateral responses over a wide range of amplitudes. This configuration is selected to promote global extension of the leg Time Specificity: Determination of Stimulation Patterns The required timing for each type of stimulation is determined. Prior to the planned experiments, first EMG recordings of a few healthy individuals walking in the same conditions as used for the impaired subjects are performed. From these EMG recordings, the spatiotemporal maps (i.e. digital characteristic maps) of motoneuron activation during healthy locomotion are computed and determined. In rats and primates or humas, the analysis of these spinal maps will reveal that the spinal segments associated with flexion should be activated from the beginning of swing (foot off) to the middle of swing. Similarly, the spinal segments associated with extension should be activated from the beginning of stance ('foot strike') to the middle of stance.

Then, a system is set up, which is able to detect or predict in real-time the gait events necessary for spatiotemporal neuromodulation: "foot off", "foot strike", "mid-stance", "mid-swing". This system can be based on a real-time motion capture system in case there is residual voluntary motor control and if the animal can wear infrared-reflective markers or other types of motion sensors. Otherwise, the instantaneous motor state can be decoded from neural signals using intracortical microelectrode arrays, electro encephalograms (EEG) or implanted EEG (Ecog).

Following to that, the sequence of stimulation bursts is programmed based on the detected gait events. In case all the detected events are sufficiently separated in time, all of them can be used to trigger the onset or the end of a particular set of stimulation bursts. However, if the stimulator can only accept stimulation commands up to a maximum rate and if the time interval between some consecutive events is too short to send two separate commands, an alternative solution is to pre-program the duration of the stimulation bursts. In this solution, the gait events only trigger the onset of stimulation, and the bursts are terminated automatically after a certain time has elapsed.

In a further step, initial amplitudes and frequencies are selected. To start with this procedure, e.g. one can select a frequency of about 60 Hz for all electrode configurations used in the program defined above. For each electrode configuration, one can select an amplitude around 1.5 times the motor threshold obtained during recruitment curves. Closed-loop spatiotemporal neuromodulation may be tested with this set of parameters. The amplitudes may be adjusted based on kinematics and EMG activity. Each electrode configuration should have a significant effect on the targeted muscle group without loss of muscle specificity.

The stimulation timing may be refined empirically. Alternatively, this can be done automatically with simulation tools or the like.

One may anticipate or delay the onset of each stimulation burst and see if the effect on kinematics and EMG activity is improved. Kinematic effects can be quantified by looking at key variables such as step height or stride length, or by computing an exhaustive list of kinematic variables and using dimensionality reduction techniques such as Principal Component Analysis (PCA). Similarly, one may extend or reduce the duration of each stimulation burst and examine the effect on kinematics and EMG activity. The process may be iterated until an optimal set of parameters is found.

Also, stimulation amplitudes and frequencies may be refined. The timing obtained in the previous step may be used. One may then re-adjust the amplitudes and frequencies. Each electrode configuration should have a significant effect on the targeted muscle group without loss of muscle specificity.

Automatic Procedure—Spinal Map Computation

Locomotion is a basic motor activity that requires the coordination of many limb and trunk muscles. Muscle activity is a reflection of the α-motoneurons firing on segments of the spinal cord. The algorithm uses recordings of muscle activity (EMG) to construct maps of spinal α-motoneuron activity by adding up the contributions of each muscle to the total activity in each spinal segment, referred as "spinal maps". Spinal maps are computed independently for both legs. Myotomal maps are used to determine the approximate rostro-caudal location of α-motoneurons pools in the subject's spinal cord, and to map the recorded patterns of muscle activity. Spinal maps provide information regarding location, duration and intensity of the activation of α-motoneurons during the execution of a locomotor task.

The pathological spinal cord map 49 comprises information about the α-motoneuron activation of the spinal cord.

The information about the α-motoneuron activation of the spinal cord is calculation by means of an activation function as weighted sum of the EMGs of segments of the spinal cord, using myotomal maps as weights.

Figure 7:
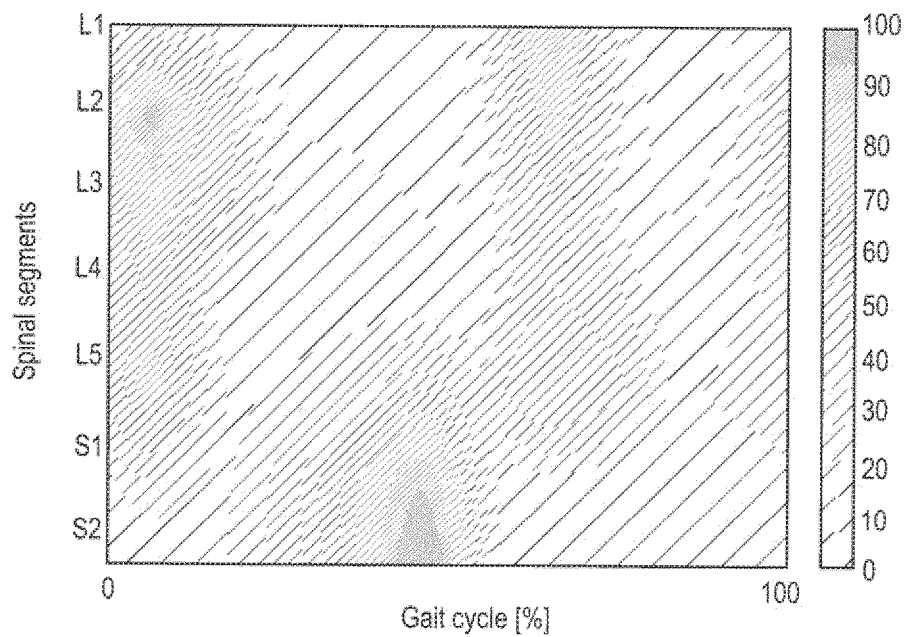
FIG. 7 a healthy spinal map.

FIG. 7 shows a healthy spinal map.

Figure 8:
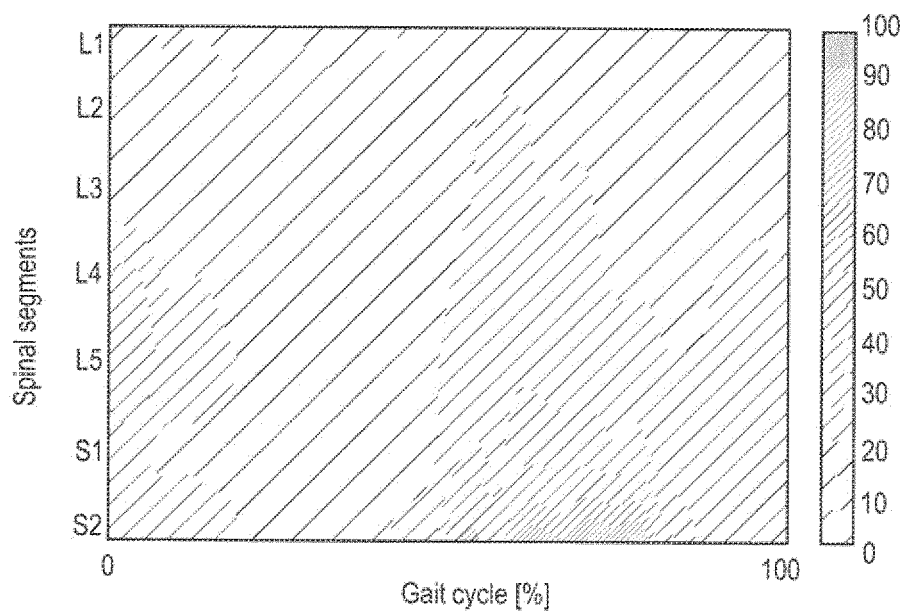
FIG. 8 a injured spinal map.

FIG. 8 shows a injured spinal map.

An averaged map over the locomotor task cycles (i.e. gait cycles) is computed to extract the average activity. A reference spinal map (RSM) 51 is computed from the locomotion of healthy subjects (FIG. 7) and the injured spinal map (ISM) 49 is extracted by the locomotion of the impaired subject (FIG. 8). Numerical difference between RSM and ISM provides a differential map (DSM), computed by means of the computer 16 and the analysis module 42 and the compensation module 52, which shows the missing activation focuses on the subject's spinal cord. The DSM represents the stimulation strategy to apply using EES.

The algorithm collects a wide spectrum of activations of the α-motoneurons by stimulating the spinal cord with several protocols. Each protocol incorporates different values of the stimulation parameters (i.e. amplitude, frequency, pulsewidth, stimulation onset, stimulation duration, an electrodes location).

Finally, the algorithm selects the stimulation protocols able to replicate the DSM. The same approach is applied to both the legs.

The stimulation strategy is based on the difference of the spatiotemporal maps of α-motoneuron (MN) activation in the spinal cord between healthy and injured subjects while performing a locomotor task. The estimation of EES parameters that best reconstruct the missing α-motoneuron activation may increase the effectiveness of EES-based therapies.

The algorithm is composed of two separate steps. The first "Functional mapping" step takes place soon after the implantation of the multi-electrode arrays for EES. The aim is to measure the α-motoneuron activation elicited by stimulation over each electrode of each array. Elicited α-motoneuron activation is measured indirectly by normalizing the stimulation-induced EMG activity using a scaling matrix obtained from the anatomical distribution of α-motoneuron pools over the spinal cord. Ideally, functional mapping should provide the stimulation-mediated increase in α-motoneuron activation for all combinations of stimulation parameters.

The second "Parameter estimation" step, given the limitations of the stimulation control and delivery system, will determine the stimulation parameters of EES protocols. The algorithm will use the information on α-motoneuron activation acquired during the functional mapping to design the EES protocols that best generate the difference between the average healthy and subject's dysfunctional spatiotemporal maps of α-motoneuron activation over the task execution.

However, since the α-motoneuron activation depends on the current state of the network and its inputs, selection of stimulation parameters should be performed in an environment that best resembles the use-case. For example, measuring the EMG responses to EES while the subject attempts to walk on a treadmill assisted by a body-weight support robot will provide a more relevant estimate of stimulation-mediated increase in α-motoneuron activation than measuring the responses while the subject lies supine on a table. Hence, based on the available time and on the subject's locomotor abilities, there are two possible options for elaborating the optimal stimulation strategy. The two options differentiate based on the parameters to estimate during the two steps of the algorithm.

Spinal Map Computation

Recordings of muscle activity are used to construct maps of spinal MN activity by adding up the contributions of each muscle to the total activity in each spinal segment. EMG data are high pass filtered, rectified and low pass filtered to obtain an envelope that represents the muscle activity. The assumption is that the EMG envelope provides an indirect measure of the net firing of motoneurons of that muscle in the spinal cord. The muscle activity is then normalized by its maximal activation recorded by high amplitude stimulation of the spinal cord. Myotomal innervation patterns are used to define the approximate rostro-caudal location of MN pools in the spinal cord. They define the relative percentage contribution of individual spinal roots in the motor responses. We can use this relationship to convert the normalized muscle activity into relative activity of MN within a given segment using the following formula:

$$S_i = \frac{\sum_{j=1}^{n_i} W_j * EMG_j}{\sum_{j=1}^{n_i} W_j}$$

where $S_i$ is the MN activation in the i-th spinal segment, $n_i$ is the number of $EMG_j$s corresponding to the i-th segment, $EMG_j$ represents the normalized muscle activity, $W_j$ is the percentage of contribution of the muscle j in the i-th spinal segment. This analysis provides information regarding location, duration and intensity of activation during walking. Finally, averaging the activity for each leg over the locomotor task cycles (i.e. foot strike to foot strike during the gait cycle) defines the phases of MN activity. The spinal map is computed for both healthy and injured conditions.

Figure 9A:
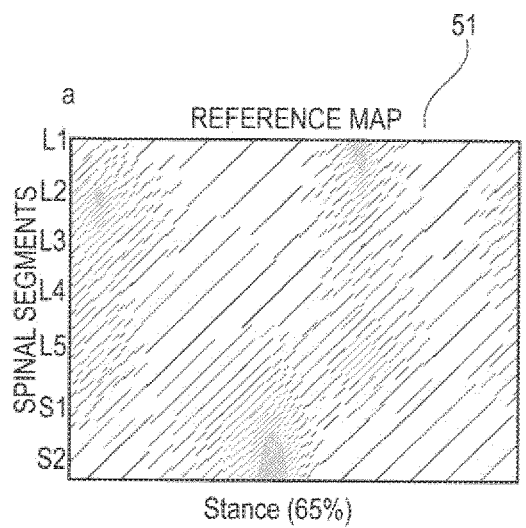
FIG. 9a (average) spatiotemporal MN activation map from healthy people.

FIG. 9a shows an average spatiotemporal MN activation map from healthy people, i.e. a reference map 51 stored in the healthy spinal cord map storage module 50.

Figure 9B:
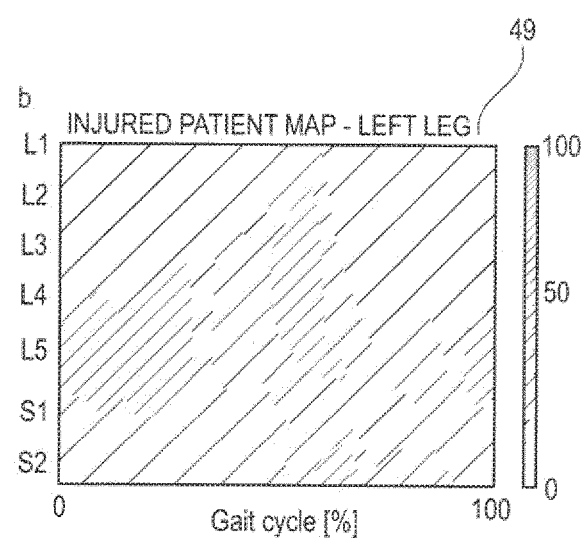
FIG. 9b spatiotemporal MN activation map from a person with SCI.

FIG. 9b shows a spatiotemporal MN activation map from a person with SCI, i.e. an example of a pathological spinal cord map 49 stored in the pathological spinal cord map storage module 48.

For example, average MN activation spinal maps of 13 healthy individuals and a person with SCI are shown in FIG. 9a and FIG. 9b, respectively.

The map of the person with SCI is computed e.g. by means of the computer 16 from EMG recordings during overground walking using a body weight support robot, in absence of stimulation. The two maps show a strong difference in activation. The average healthy map reveals a cyclical sequence of MN activation bursts: knee extension and ankle plantar flexion during initial and middle parts of the stance, hip flexion and ankle dorsiflexion in early swing, followed by knee extension in late swing. A person with SCI does not show these bursts of MN activation during the gait cycle.

Functional Mapping

Functional mapping aims to determine the spatial distribution of α-motoneuron activation evoked by stimulation delivered over each electrode of the arrays implanted on the subject. All active sites should be tested in order to measure the relationship between stimulation parameters and induced muscles activation. Moreover, in order to determine the maximum muscle activation for normalization purpose, the stimulation amplitude should be increased until the muscle recruitment has saturated. Functional mapping finally provides a spectrum of possible activations over the spinal segments and represents the basis for building an effective stimulation pattern during walking tasks.

However, since the α-motoneuron activation depends on the current state of the network and its inputs, selection of stimulation parameters should be performed in an environment that best resembles the use-case. For example, EES protocols are performed while the subject is attempting to walk on a treadmill assisted by a body-weight support robot. Hence, based on the subject's locomotor abilities, there are two possible options for elaborating the spinal activation induced by stimulation.

Option 1:

Functional mapping is performed while the injured subject is attempting to walk on a treadmill assisted by a body-weight support robot. Stimulation is delivered constantly through a selected electrode, or electrode pairs, to elicit activity of leg muscles. This configuration allows the variation of all stimulation parameters (frequency, amplitude, pulse width, and timing) and the observation of the related spinal MN activations.

Option 2:

Functional mapping is performed while the injured subject is lying supine on a bed. Stimulation is delivered in one to two minute blocks. In each block, single-pulses of cathodic monopolar and bipolar, charge-balanced stimulation delivered through a selected electrode or electrode pairs are used to elicit activity of leg muscles. During the block, a new stimulation pulse is sent every is or 0.5 s. Spacing the stimulation pulses by at least 0.5 s, the muscle responses to individual stimulation pulses can be dissociated from their predecessors and successors. The stimulation amplitude increases over a given range after 4-6 repetitions of the same amplitude. This configuration does not allow the variation of all stimulation parameters. In fact, frequency of stimulation remains unchanged (1 Hz). However, this setup allows the observation of the spinal MN activations induced by each electrode array.

Figure 10A:
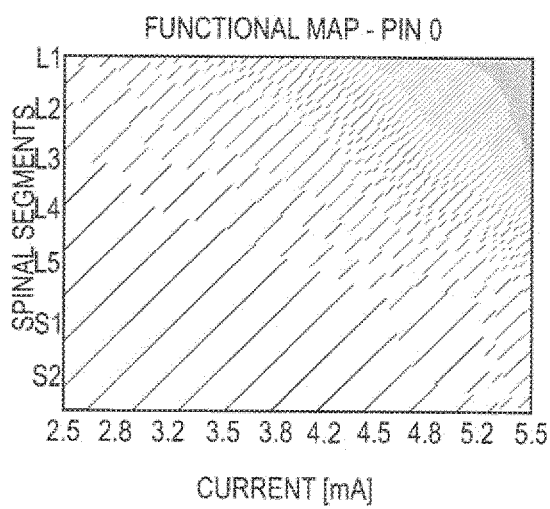
FIG. 10a, b activation of α-motoneuron following single-pulses stimulation during functional mapping.
Figure 10B:
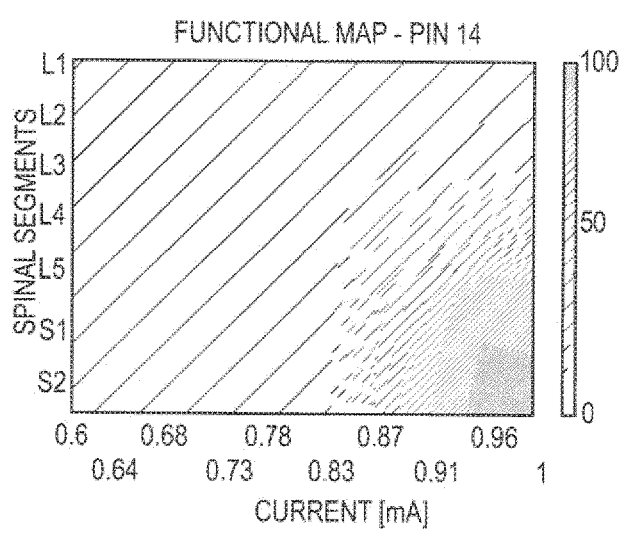

The result of functional mapping is the spectrum of the α-motoneuron activations over the spinal cord segments, where each activation is related to a different stimulation configuration (FIGS. 10a and 10b; left (i.e. FIG. 10a) and right (i.e. FIG. 10b) show the effects driven by stimulation on different pins of the implanted array with ten different current amplitudes). However, the afferent information to the spinal network in the second option does not resemble the information provided in the use-case. Therefore, further exploration of spinal activation will be performed in the second step of the algorithm.

Stimulation Pattern Detection Algorithm

The goal of the stimulation pattern detection algorithm is to define the stimulation strategy that, superimposed onto the altered MN activation map of the subject with impairment, replicates the healthy MN activation map. Consequently, computing the difference between the healthy and altered activation maps by means of the computer 16 and the analysis module 42 and the compensation module 52 will dictate the stimulation strategy. The resulting differential map shows the absent MN activation phases that should be reproduced using the stimulation.

The stimulation strategy aims to reproduce the missing MN activation phases. Prior information of α-motoneuron activation acquired during the functional mapping is used to compute the stimulation protocols that best reproduce the missing MN activation phases. However, as described earlier, depending on the chosen setup functional mapping dataset different information is provided. Therefore, there are two possible ways to compute the optimal stimulation strategy.

Option 1:

The functional mapping dataset can directly be used to compute by means of the computer 16 and the analysis module 42 and the compensation module 52 the stimulation pattern detection algorithm. As the functional mapping dataset was acquired during a locomotor task, it directly provides the spinal MN activations induced by different stimulation protocols.

Option 2:

The functional mapping dataset provides the information about the electrodes of the neuromodulation lead 22 to use in order to best fit the missing spinal MN activations. However, since the functional mapping dataset provides no information regarding the amplitude and frequency of stimulation, these parameters should be estimated during the execution of the locomotor task. In fact, the afferent information to the spinal network strongly affects the MN activation. Stimulation is delivered constantly through the previously selected electrode while the injured subject is attempting to walk on a treadmill assisted by a body-weight support robot. This configuration allows the variation of stimulation amplitude and frequency and the observation of the related spinal MN activations. Finally, the acquired spinal MN activations are used to compute the stimulation pattern detection algorithm.

The stimulation pattern detection algorithm aims to reproduce the missing MN activation phases. Missing activations are extrapolated by segmentation of the differential MN activation map. Depending on the complexity of the stimulation strategy to be applied, activation phases can be highly or sparsely segmented.

Figure 11:
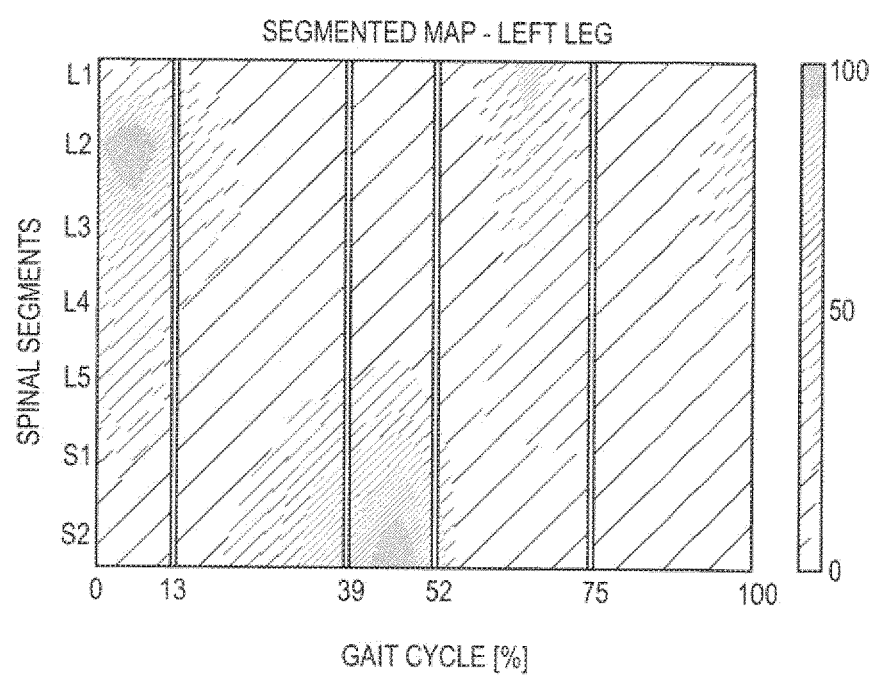
FIG. 11 a sparse segmentation approach.

A sparse segmentation approach is shown on FIG. 11. Segmentation reduces the MN-activation differential map to a set of one-dimensional arrays. Each array ($A_k$) contains the maximal MN-activation value over all spinal segments within the associated temporal segment. Secondly, a discrete linear combination of the previously obtained (option 1 or option 2) MN activations ($\hat{A}$) is performed in order to replicate the maximal activation on pre-selected segments.

In other words:

The compensation module 52 is configured and arranged such that the neurostimulation protocol is calculated such that the neurostimulation protocol superimposed on the pathological spinal cord map 49 replicates the reference map.

The pathological spinal cord map 49 and the reference map 51 comprise information about a movement, especially a sequence of movements like e.g. a gait cycle.

The compensation module 52 is configured and arranged such that related to the movement the pathological spinal cord map 49 and/or the reference map 51 can be segmented for calculation of the compensation.

Also, the compensation module 52 is further configured and arranged such that from the segmented pathological spinal cord map 49 and the segmented the reference map 51 the segments with the highest deviation are identified to create a distance matrix for the compensation.

The electrode selection is performed by differentiating the activations of the segmented gait phase and of the stimulation configuration selected during functional mapping, assigning a fitting rate (FR) based on the Euclidean norm of the difference.

$$FR_k(el, amp, freq, pw) = \|A_k - \hat{A}(el, amp, freq, pw)\|$$

where k is the k-th segmented gait phase, el is the electrode position used during stimulation, amp is the stimulation amplitude, freq is the stimulation frequency, pw is the stimulation pulsewidth.

The FR is an expression of the ability of the performed stimulation to mimic the required activation. Furthermore the algorithm takes into account the effects that the stimulation over a pin has on the contralateral side. Contralateral activation (CA) is computed as the MN activation $\tilde{A}$(el, amp, freq, pw) obtained during functional mapping on the contralateral leg, i.e. as considering any activation on the contralateral leg as counterproductive.

$$CA_k(el, amp, freq, pw) = \|\tilde{A}(el, amp, freq, pw)\|$$

Finally, "effectiveness" of stimulation is the capacity to fit the desired ipsilateral activation without stimulating the contralateral side. A weighting function describing the effectiveness of the stimulation is applied between FR and CA, and is expressed by the following formula:

$$effectiveness_k(el, amp, freq, pw) =$$
$$\alpha * FR_k(el, amp, freq, pw) + (1 - \alpha) * CA_k(el, amp, freq, pw)$$
$$(el_k, amp_k, freq_k, pw_k) = \underset{el, amp, freq, pw}{\operatorname{argmin}} (effectiveness_k)$$

where α is a parameter that regulate the relevance of a FR compared to CA. The function outcome selects the stimulation configuration for the considered gait phase with the associated parameters (el, amp, freq, pw).

Finally, the result of the analysis is a sequence of EES protocols, one for each segmented phase. The timing and duration of each EES protocol is defined by the temporal segmentation: the start and duration of the protocol is equal to the start and duration of the temporal segment.

Note that the example control and estimation routines included herein can be used with various neuromodulation and/or neurostimulation system configurations. The control methods and routines disclosed herein may be stored as executable instructions in non-transitory memory and may be carried out by the control unit in combination with the various sensors, actuators, and other system hardware in connection with a medical neurostimulation system. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the control unit, where the described actions are carried out by executing the instructions in a system including the various hardware components in combination with a electronic control unit.

Explicitly disclosed in connection with the above disclosure is the following aspect:

1. A method for planning and/or providing neurostimulation for a patient, comprising
   comparing a pathological spinal cord map and a reference map automatically to generate a deviation map, the deviation map describing the difference between the pathological spinal cord map and the reference map, the pathological spinal cord map describing the activation of the spinal cord of a patient, and the healthy spinal cord map describing physiological activation of the spinal cord of at least one healthy subject, and
   calculating on the basis of the deviation map a neurostimulation protocol for compensating the activation difference between the pathological spinal cord map and the reference map; and
   generating a neurostimulation signal based on the neurostimulation protocol.

2. The method according to aspect 1, wherein the method includes the following steps:
   an analysis module (42) is used, which is configured and arranged such that the pathological spinal cord map and the reference map can be compared and/or analyzed automatically such that a deviation map is created, the deviation map describing the difference between the pathological spinal cord map and the reference map, and
   a compensation module (52) which is configured and arranged to calculate on the basis of the deviation map a neurostimulation protocol for compensating the activation difference between the pathological spinal cord map and the reference map.

3. The method according to aspect 2, wherein the method is a self-learning or machine-learning process.

REFERENCES 10 neuromodulation and/or neurostimulation system
12 physiological response measurement sensor
14 physiological response measurement receiver and processor
16 computer
18 software
20 visualization module
22 neuromodulation lead
24 neuromodulation pulse generator
26 first data input module
28 stimulation related basic data storage module
30 second data input module
32 stimulation related response data storage module
34 transfer module
36 digital characteristic map
38 mapping module
40 virtual mapping module
42 correlation and/or simulation module, analysis module
44 neuromodulation settings generation module
46 transfer interface
48 pathological spinal cord map storage module
49 pathological spinal cord map
50 healthy spinal cord map storage module
51 reference map 52 compensation module
M1 first muscle
M2 second muscle
P patient
P1 onset point
P2 saturation point
P3 specificity point
P1' onset point
P2' saturation point
S storage

The invention claimed is:

1. A system for planning and/or providing neurostimulation for a patient, comprising:
   a pathological spinal cord map storage module for storing at least one pathological spinal cord map describing activation of a spinal cord of the patient,
   a healthy spinal cord map storage module for storing at least one reference map describing physiological activation of a healthy spinal cord of at least one healthy subject,
   an analysis module configured and arranged such that the pathological spinal cord map and the at least one reference map can be compared and/or analyzed automatically such that a deviation map is created, the deviation map describing an activation difference between the pathological spinal cord map and the at least one reference map, and
   a compensation module which is configured and arranged to calculate on a basis of the deviation map a neurostimulation protocol for compensating the activation difference between the pathological spinal cord map and the reference map.

2. The system according to claim 1, wherein the pathological spinal cord map comprises information about an a-motoneuron activation of the spinal cord.

3. The system according to claim 2, wherein the information about the a-motoneuron activation of the spinal cord is calculated based on an activation function as weighted sum of electromyography (EMG) data of segments of the spinal cord, using myotomal maps as weights.

4. The system according to claim 1, wherein the compensation module is configured and arranged such that the neurostimulation protocol is calculated such that the neurostimulation protocol superimposed on the pathological spinal cord map replicates the reference map.

5. The system according to claim 1, wherein the pathological spinal cord map and the reference map comprise information about a sequence of movements.

6. The system according to claim 5, wherein the compensation module is configured and arranged such that based on the sequence of movements, the pathological spinal cord map and/or the reference map is segmented for calculation of the neurostimulation protocol for compensation.

7. The system according to claim 6, wherein the compensation module is further configured and arranged such that from the segmented pathological spinal cord map and the segmented the reference map the segments with the highest deviation are identified to create a distance matrix for the neurostimulation protocol for compensation.

8. The system according to claim 1, further comprising a stimulation related basic data storage module for storing stimulation related basic data defining parameters of a neurostimulation system for treating a patient, the stimulation related basic data storage module comprising at least one set of stimulation related basic data.

9. The system according to claim 1, further comprising a stimulation related response data storage module for storing stimulation related response data of neurostimulation provided to the patient, the stimulation related response data storage module comprising at least one set of stimulation related response data including activation of the spinal cord as response to the stimulation.

10. The system according to claim 9, further comprising a transfer data storage module for storing the transfer data, wherein the transfer data comprise artificial response data and/or link data and/or translation data, which link and/or translate at least partially the stimulation related basic data and the stimulation related response data with each other, the transfer data storage module comprising at least one set of transfer data and a mapping module configured and arranged such that based on the stimulation related basic data and stimulation related response data and the transfer data a digital characteristic map is generated and/or stored, which describes an interrelation between the stimulation related basic data and the stimulation related response data and the transfer data.

11. The system according to claim 10, further comprising a stimulation related response data input module and wherein the system is configured and arranged such that an inverse control is provided by inputting the stimulation related response data via the stimulation related response data input module and the system further comprising a selection module, which is configured and arranged such that based on the digital characteristic map and the deviation map, suitable stimulation related basic data are selected.

12. The system according to claim 10, further comprising a neuromodulation settings generation module, which is configured and arranged to translate the digital characteristic map and the deviation map into neuromodulation parameter settings for a neuromodulation treatment of the patient.

13. A method for planning and/or providing neurostimulation for a patient, comprising at least the following steps:
   obtaining at least one pathological spinal cord map describing an activation of a spinal cord of the patient,
   obtaining at least one reference map describing physiological activation of a healthy spinal cord of at least one healthy subject,
   comparing and/or analyzing the pathological spinal cord map and the reference map to create a deviation map, wherein the deviation map describing an activation difference between the pathological spinal cord map and the reference map, and
   calculating on the basis of the deviation map a neurostimulation protocol for compensating the activation difference between the pathological spinal cord map and the reference map.

14. The method of claim 13, wherein the method is completely done in-vitro without connection to the patient.

15. The method of claim 14, wherein the method is performed offline based on separately obtained patient data.

* * * * *